US011766382B2

(12) United States Patent
Sedic

(10) Patent No.: US 11,766,382 B2
(45) Date of Patent: *Sep. 26, 2023

(54) SKINCARE DEVICES AND METHODS OF USE

(71) Applicant: FOREO Inc., Las Vegas, NV (US)

(72) Inventor: Filip Sedic, Stockholm (SE)

(73) Assignee: FOREO Inc., Las Vegas, NV (US)

( * ) Notice: Subject to any disclaimer, the term of this patent is extended or adjusted under 35 U.S.C. 154(b) by 831 days.

This patent is subject to a terminal disclaimer.

(21) Appl. No.: 16/390,305

(22) Filed: Apr. 22, 2019

(65) Prior Publication Data

US 2019/0240110 A1 Aug. 8, 2019

Related U.S. Application Data

(63) Continuation of application No. 16/175,260, filed on Oct. 30, 2018, now Pat. No. 10,307,330.

(Continued)

(51) Int. Cl.
*A61H 23/02* (2006.01)
*A45D 34/04* (2006.01)
(Continued)

(52) U.S. Cl.
CPC ............. *A61H 23/02* (2013.01); *A45D 34/04* (2013.01); *A45D 44/00* (2013.01); *A45D 44/002* (2013.01); *A61F 7/00* (2013.01); *A61H 23/0254* (2013.01); *A61N 5/0616* (2013.01); *A45D 2200/155* (2013.01); *A45D 2200/205* (2013.01); *A45D 2200/207* (2013.01); *A45D 2200/25* (2013.01); *A61H 2201/0153* (2013.01); *A61H 2201/0176* (2013.01); *A61H 2201/0188* (2013.01);
(Continued)

(58) Field of Classification Search
CPC . A61H 23/02; A61H 23/0218; A61H 23/0245
See application file for complete search history.

(56) References Cited

U.S. PATENT DOCUMENTS 3,467,080 A 9/1969 McNair
3,585,990 A 6/1971 Blachly et al.
(Continued)

FOREIGN PATENT DOCUMENTS

CN 201085727 7/2008
CN 105126257 12/2015
(Continued)

OTHER PUBLICATIONS

Clinique, "Clinique Sonic System Massaging Treatment Applicator," Clinique.com, pp. 1-4, https://www.clinique.com/product/15676/37504/skin-care/sculptwear/clinique-sonic-system-massaging-treatment-applicator, accessed Jul. 2017.
(Continued)

*Primary Examiner* — Michael J Tsai
(74) *Attorney, Agent, or Firm* — Evan Feldstein

(57) ABSTRACT

An example skincare device includes a main body having a first side, a second side, an intermediate portion, a groove, a light source, a motor, a temperature control unit, and a user control configured to control one or more of the light source, motor, and temperature control unit. The skincare device can provide heat, cool, light, and/or vibrational therapy to a user's skin.

12 Claims, 27 Drawing Sheets

Related U.S. Application Data

(60) Provisional application No. 62/586,994, filed on Nov. 16, 2017.

(51) Int. Cl.
*A61N 5/06* (2006.01)
*A45D 44/00* (2006.01)
*A61F 7/00* (2006.01)

(52) U.S. Cl.
CPC ............... *A61H 2201/0207* (2013.01); *A61H 2201/0214* (2013.01); *A61H 2201/10* (2013.01); *A61H 2201/1215* (2013.01); *A61H 2201/165* (2013.01); *A61H 2201/169* (2013.01); *A61H 2201/50* (2013.01); *A61H 2201/5007* (2013.01); *A61H 2201/5023* (2013.01); *A61H 2201/5025* (2013.01); *A61H 2201/5035* (2013.01); *A61H 2201/5082* (2013.01); *A61H 2201/5097* (2013.01); *A61H 2205/022* (2013.01); *A61H 2205/04* (2013.01); *A61N 2005/0626* (2013.01); *A61N 2005/0651* (2013.01); *A61N 2005/0652* (2013.01); *A61N 2005/0663* (2013.01)

(56) References Cited

U.S. PATENT DOCUMENTS

| | | | | |
|---|---|---|---|---|
| 3,828,769 | A * | 8/1974 | Mettler | A61H 23/0245 601/2 |
| 4,757,806 | A * | 7/1988 | Muchisky | A61H 23/0263 601/87 |
| 5,176,130 | A * | 1/1993 | Kim | A61H 23/02 601/73 |
| 7,914,523 | B2 | 3/2011 | Barolet et al. | |
| 2003/0083720 | A1 | 5/2003 | Peterson | |
| 2003/0163068 | A1 | 8/2003 | Kang | |
| 2004/0006332 | A1 * | 1/2004 | Black | A61H 23/0245 606/9 |
| 2004/0147984 | A1 | 7/2004 | Altshuler et al. | |
| 2004/0193237 | A1 * | 9/2004 | Krueger | A61F 7/02 607/96 |
| 2005/0070827 | A1 | 3/2005 | Lee | |
| 2006/0247742 | A1 | 11/2006 | Lee | |
| 2006/0264788 | A1 * | 11/2006 | Chou | A45D 34/04 601/17 |
| 2007/0179414 | A1 * | 8/2007 | Imboden | H02J 7/025 601/72 |
| 2007/0282400 | A1 | 12/2007 | Gorham | |
| 2008/0053979 | A1 * | 3/2008 | Toya | A61H 23/0263 219/385 |
| 2008/0071138 | A1 * | 3/2008 | Mertens | A61H 19/34 600/38 |
| 2008/0282437 | A1 | 11/2008 | Park | |
| 2010/0049177 | A1 | 2/2010 | Boone, III et al. | |
| 2011/0040235 | A1 * | 2/2011 | Castel | A61F 7/00 604/20 |
| 2011/0138556 | A1 | 6/2011 | Sanchez Martinez | |
| 2011/0166486 | A1 * | 7/2011 | Kumanomido | A61H 23/0236 363/13 |
| 2011/0251523 | A1 * | 10/2011 | Kim | A61N 7/00 601/2 |
| 2012/0109043 | A1 * | 5/2012 | Zhou | A61H 23/0245 604/20 |
| 2013/0066404 | A1 | 3/2013 | Tapper et al. | |
| 2014/0163437 | A1 | 6/2014 | Mack et al. | |
| 2014/0276248 | A1 | 9/2014 | Hall et al. | |
| 2016/0030279 | A1 * | 2/2016 | Driscoll | A61H 19/40 601/46 |
| 2016/0331308 | A1 * | 11/2016 | Zhou | A61M 35/003 |
| 2016/0361563 | A1 * | 12/2016 | Wang | H05K 5/0086 |
| 2017/0035649 | A1 * | 2/2017 | Choi | A61H 23/0236 |

FOREIGN PATENT DOCUMENTS

| | | |
|---|---|---|
| CN | 205758949 | 12/2016 |
| CN | 206167649 | 5/2017 |
| CN | 206621528 | 11/2017 |
| JP | 2004194850 | 7/2004 |
| JP | 2005237721 | 9/2005 |
| JP | 2013146534 | 8/2013 |
| JP | 2016521999 | 7/2016 |
| JP | 201712513 | 1/2017 |
| JP | 201712628 | 1/2017 |
| JP | 2017070661 | 4/2017 |
| KR | 20130109835 | 10/2013 |
| KR | 20170108530 | 9/2017 |
| WO | 8801520 | 3/1988 |
| WO | WO2005046793 | 5/2005 |

OTHER PUBLICATIONS

Neutrogena, "Light Therapy Acne Mask," Neutrogena.com, pp. 1-9, https://www.neutrogena.com/skin/skin-acne/light-therapy-acne-mask/6810124.html, accessed Jul. 2017.
Amazon, "Panasonic Ion Effector EH-ST51-P (Pink)," Amazon.com, pp. 1-5, https://www.amazon.com/Panasonic-Ion-Effector-EH-ST51-P-Pink/dp/B00F7YSOQ, accessed Jul. 2017.
Wired Beauty, "Mapo(R) Hyrda," Wired-beauty.com, pp. 1-7, http://www.wired-beauty.com/hydra/, accessed Jul. 2017.
Ya-Man, "RF Beaute Photo Plus Hyper," ya-man.com, pp. 1-8, https://www.ya-man.com/en/products/rfbeautephotoplushyper/, accessed Jul. 2017.
Brazilian Patent Office, re: app. No. 1120190124390, Issued Feb. 12, 2021, pp. 1-8.
European Patent Office, "Extended European Search Report," for Int'l patent No. 18206354.5, dated Jun. 14, 2019, pp. 1-9.
International Searching Authority, "International Search Report and Written Opinion," int'l app. No. PCT/IB2018/001427, dated Apr. 28, 2019, pp. 1-9.
Japanese Patent Office, re: app. No. 2019-544064, Issued Oct. 6, 2020, pp. 1-7.
CIPO, re: app. No. 3,047,381, Issued Sep. 9, 2020, pp. 1-5.

* cited by examiner

SKINCARE DEVICES AND METHODS OF USE

CROSS-REFERENCE TO RELATED APPLICATIONS

This application is a continuation of U.S. Non-provisional Patent Application Ser. No. 16/175,260, filed Oct. 30, 2018, which claims the benefit of U.S. Provisional Patent Application No. 62/586,994, filed Nov. 16, 2017, each of which is incorporated into this disclosure in its entirety.

FIELD

The disclosure relates generally to the field of skincare devices and methods of use. More particularly, the disclosure relates to skincare devices suitable for use on the human face and body and various methods of using the same.

BACKGROUND

Skin health and appearance is an important aspect of many beauty regimens. As a person ages, his or her skin tends to develop wrinkles, sag, become rough, and/or develop various spots or marks. It is known that stimulating skin cells through various means such as through light therapy, vibration therapy, and/or through heat and cool therapy can produce positive effects on the skin. Such positive effects, for example, may include one or more of: increased collagen production, reduction of skin inflammation, reduction of acne, improvement of blood flow, tightening of the skin, and/or the destruction of bacteria.

Several devices exist which may provide light therapy, vibration therapy, heat therapy, or cool therapy to the skin. Such devices, however, typically provide only one type of therapy. Furthermore, these devices are often located in medical or cosmetic offices and use of such devices requires the assistance of another person to administer the desired treatment. In many instances, an administrator of the therapy must be licensed by a state or federal board (such as a medical or cosmetology board) or receive a certification to use such devices. Additionally, the use of such devices is often time-consuming.

A need exists, therefore, for improved skincare devices and methods of use that provide multiple forms of therapy (i.e., one or more of light, vibration, heat, and/or cool therapy), may be used quickly and easily by an individual outside of the confines of a medical or cosmetology office, and may be used without assistance.

BRIEF SUMMARY OF SELECTED EXAMPLES

Various example skincare devices and methods of use are described.

An example skincare device configured to treat the skin of a user comprises a main body having a first side having a first surface, a second side substantially opposite the first side having a second surface, and an intermediate portion extending from the first side to the second side having a third surface, a light source disposed within the main body and configured to emit light to treat said skin, the light source configured to emit the light adjacent the first side, a motor disposed within the main body and configured to produce pulsations of said skincare device, a temperature control unit disposed within the main body, the temperature control unit configured to generate heat to treat said skin and transfer the heat to the first side, and a user control disposed on the intermediate portion, the user control configured to operate the light source, the motor, and the temperature control unit.

Another example skincare device configured to treat the skin of a user comprises a main body having a first side having a first surface, a second side substantially opposite the first side having a second surface, and an intermediate portion extending from the first side to the second side having a third surface, the first side and the intermediate portion cooperatively defining a groove extending toward the second side, the second surface defining a set of protrusions, the third surface comprising silicone, a light source disposed within the main body and configured to emit light to treat said skin, the light source configured to emit the light adjacent the first side, the light source comprising an LED light, a motor disposed within the main body and configured to produce pulsations of said skincare device, a temperature control unit disposed within the main body, the temperature control unit configured to generate heat to treat said skin and to transfer the heat to the first side, a removeable locking mechanism configured to be inserted into the groove, the removeable locking mechanism being comprised of plastic, substantially annular, and substantially transparent, and a user control disposed on the intermediate portion, the user control configured to operate the light source, the motor, and the temperature control unit.

Another example skincare device configured to treat the skin of a user comprises a main body having a first side having a first surface, a second side substantially opposite the first side having a second surface, and an intermediate portion extending from the first side to the second side having a third surface, the first side and the intermediate portion defining an annular groove extending toward the second side, the second surface defining a set of protrusions comprised of metal, the third surface comprising silicone, a light source disposed within the main body and configured to emit light to treat said skin, the light source configured to emit the light adjacent the first side, the light source comprising an LED light, a motor disposed within the main body configured to produce pulsations of said skincare device, a temperature control unit disposed within the main body, the temperature control unit configured to generate heat to treat said skin and to transfer the heat to the first side, the temperature control unit configured to cool the first side of the main body in order to treat said skin, a removeable locking mechanism configured to be inserted into the groove, the removeable locking mechanism being comprised of plastic, substantially annular, and substantially transparent, a controller disposed within the main body and an interface operatively connected to the controller, the interface being configured to transmit information, and a user control disposed on the intermediate portion, the user control configured to operate the light source, the motor, and the temperature control unit.

Additional understanding of claimed devices and methods may be obtained by reviewing the detailed description of selected examples, below, with reference to the appended drawings.

Figure 1:
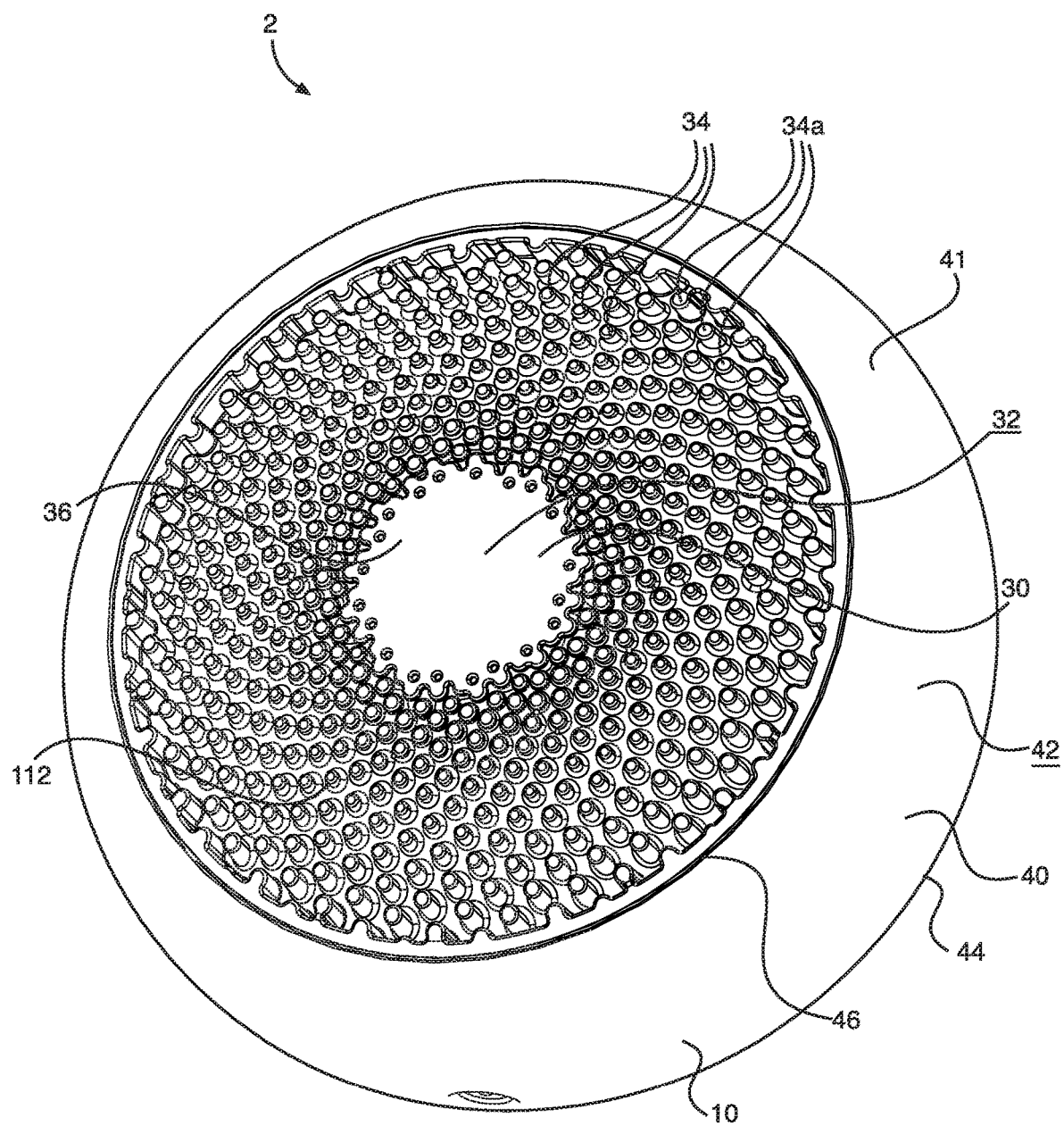
FIG. 1 is a perspective view of a first example skincare device.
Figure 2:
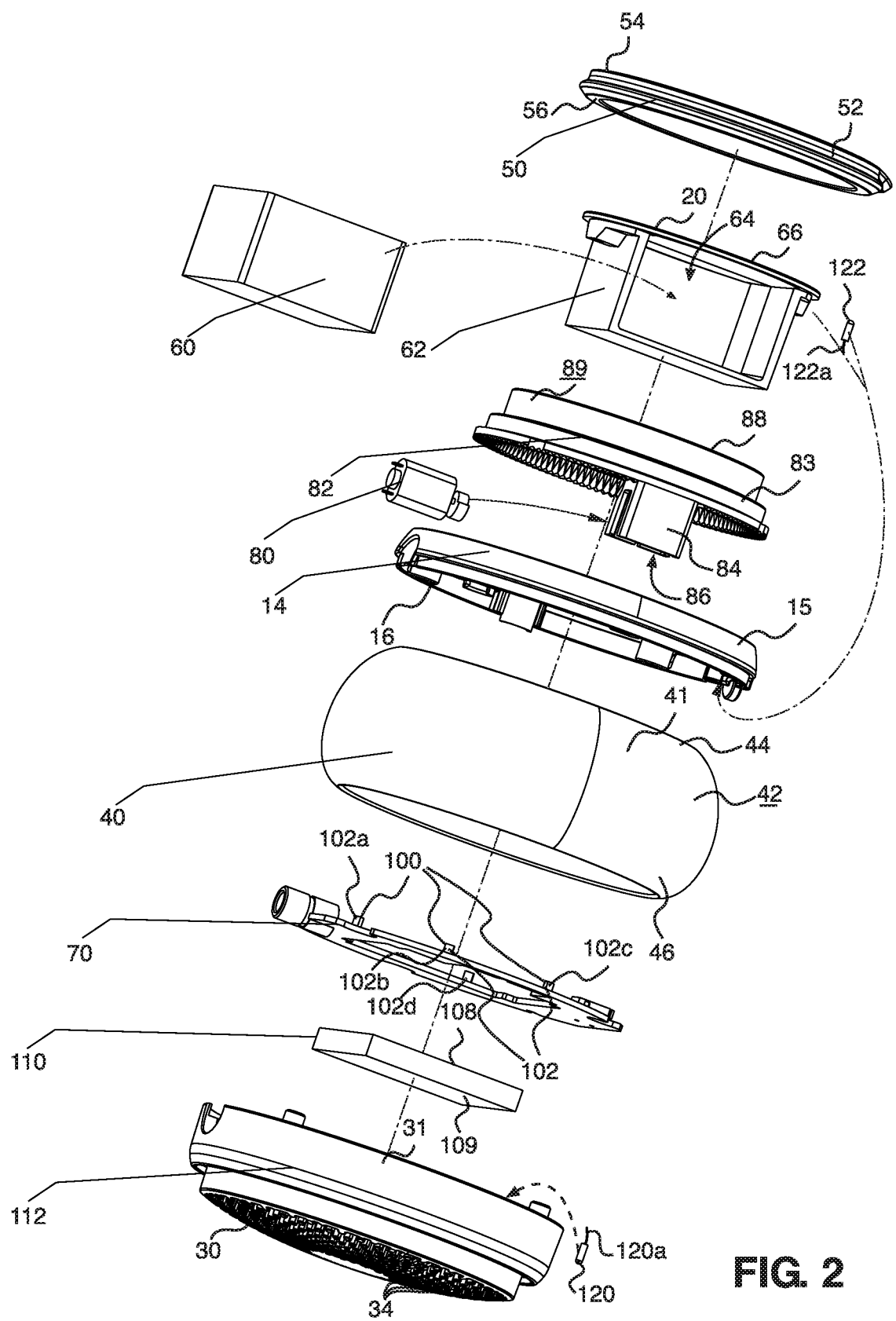
FIG. 2 is an exploded view of the skincare device illustrated in FIG. 1.
Figure 3:
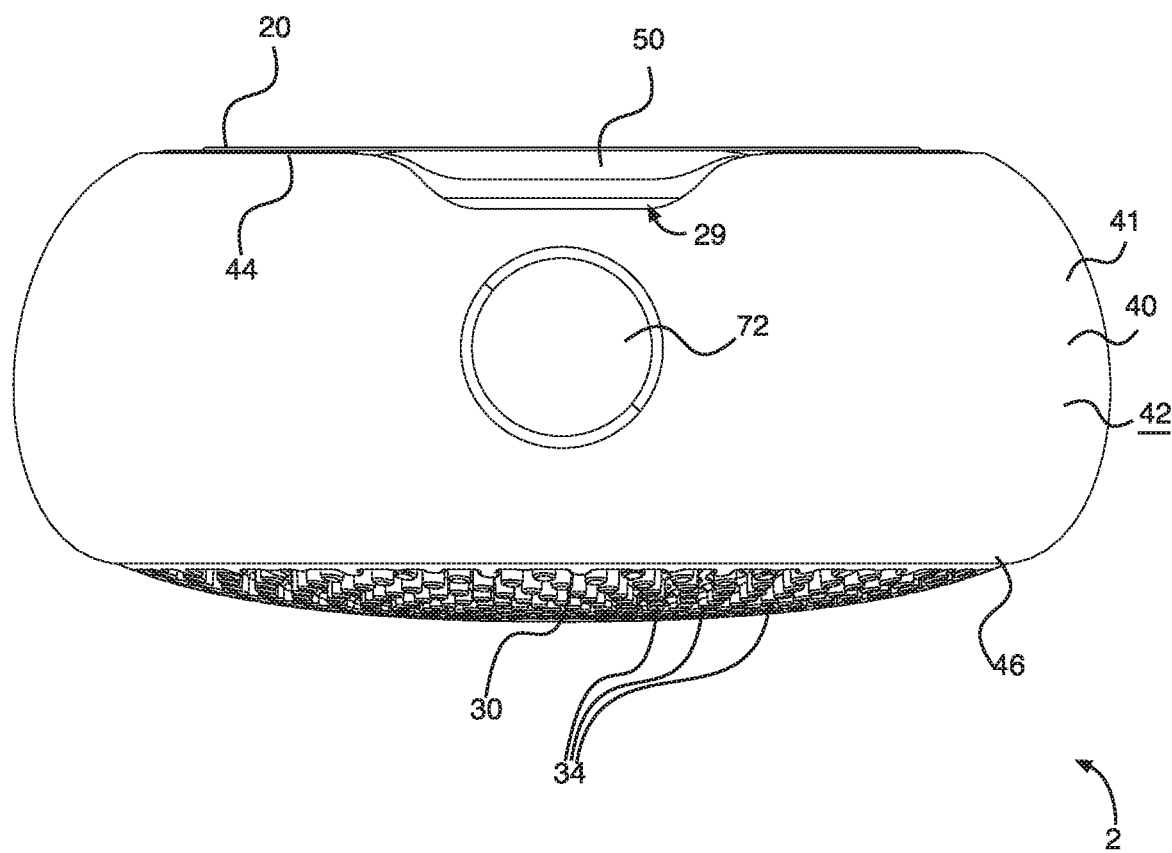
FIG. 3 is an end view of the skincare device illustrated in FIG. 1.
Figure 3A:
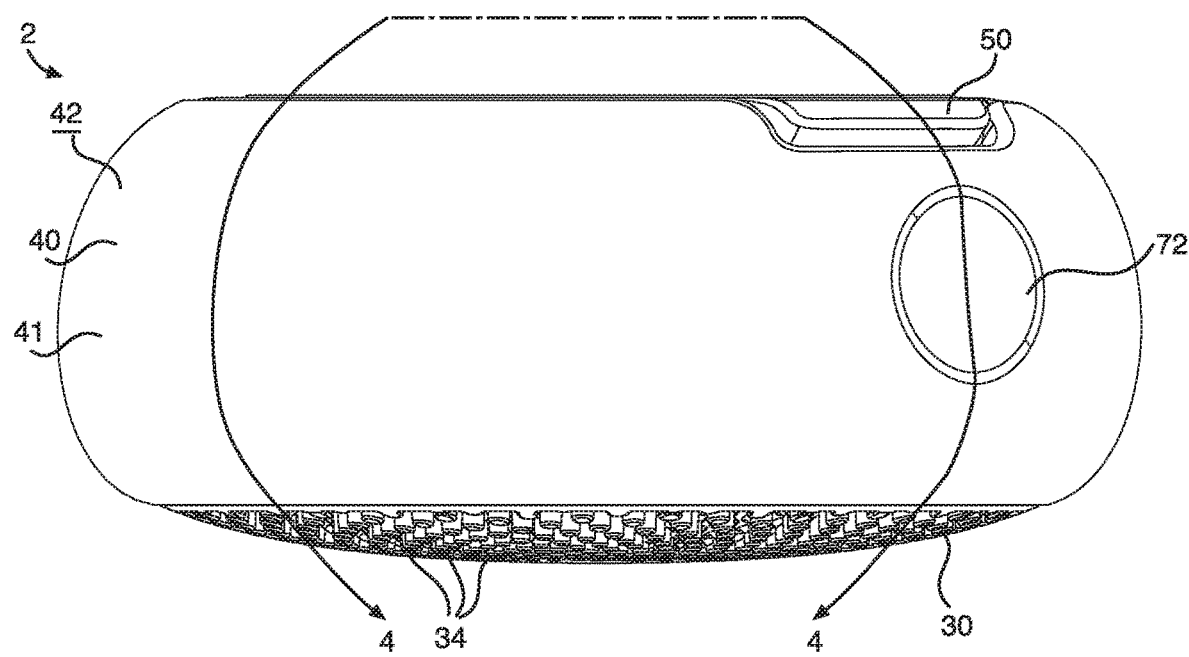
FIG. 3A is an end view of the skincare device illustrated in FIG. 3 in which the skincare device has been rotated slightly.
Figure 4:
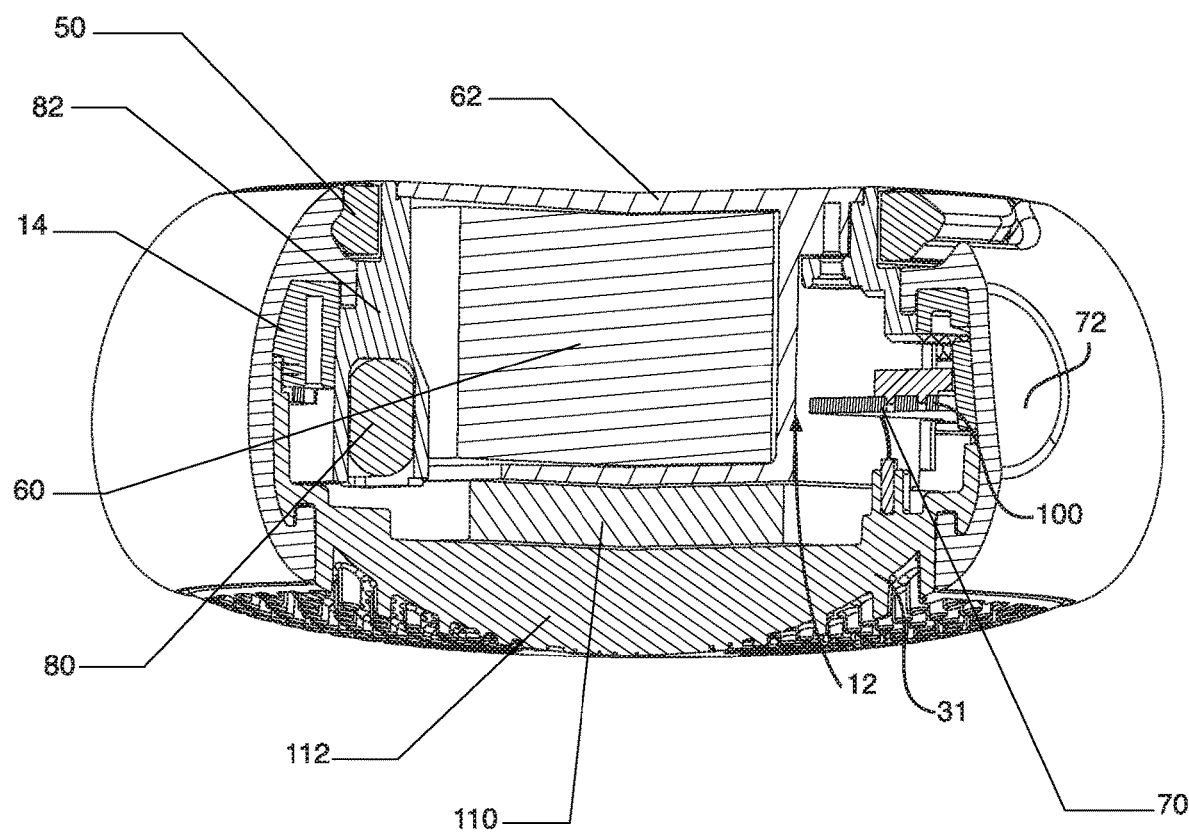
FIG. 4 is a sectional view of the skincare device illustrated in FIG. 3A, taken along line 4-4.
Figure 5:
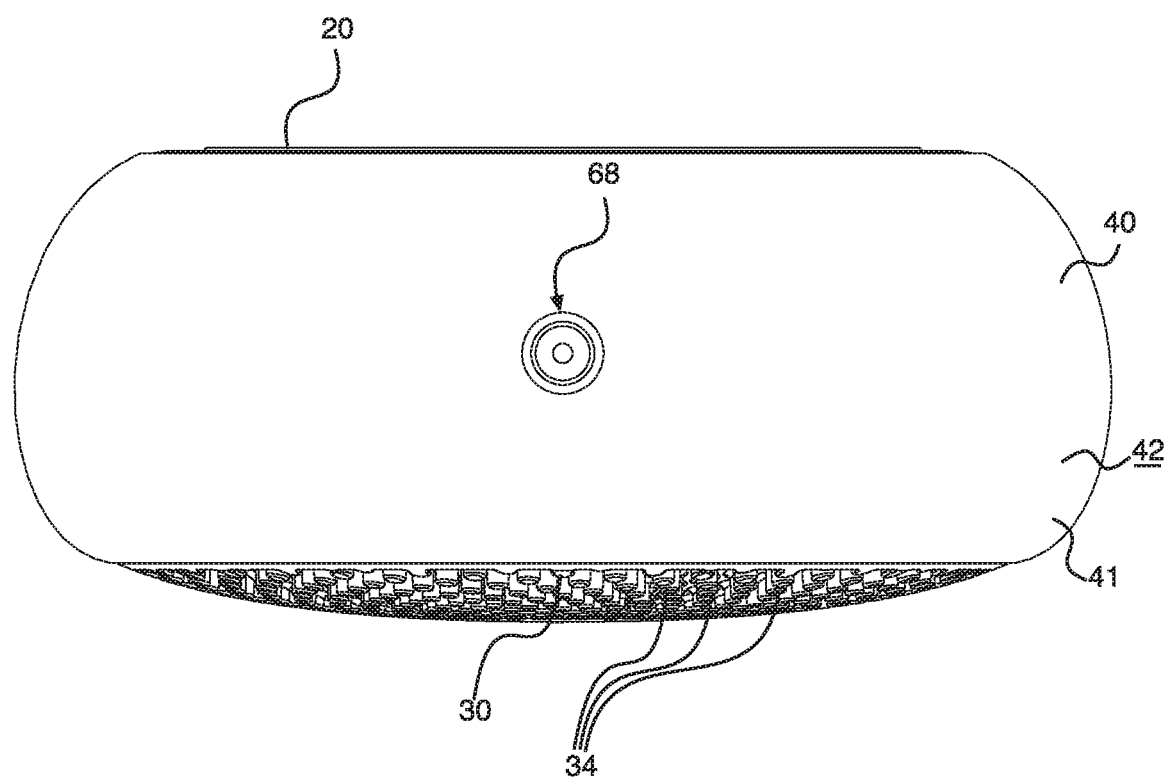
FIG. 5 is another end view of the skincare device illustrated in FIG. 1.
Figure 6:
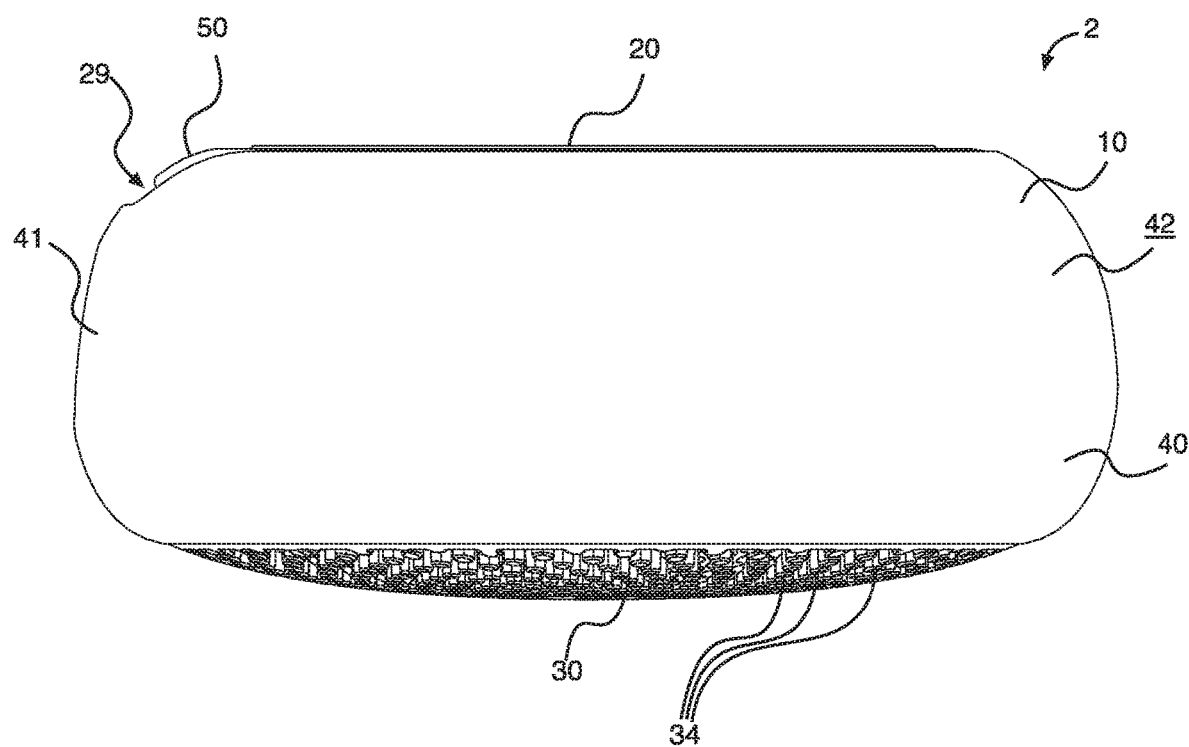
FIG. 6 is a side view of the skincare device illustrated in FIG. 1.
Figure 7:
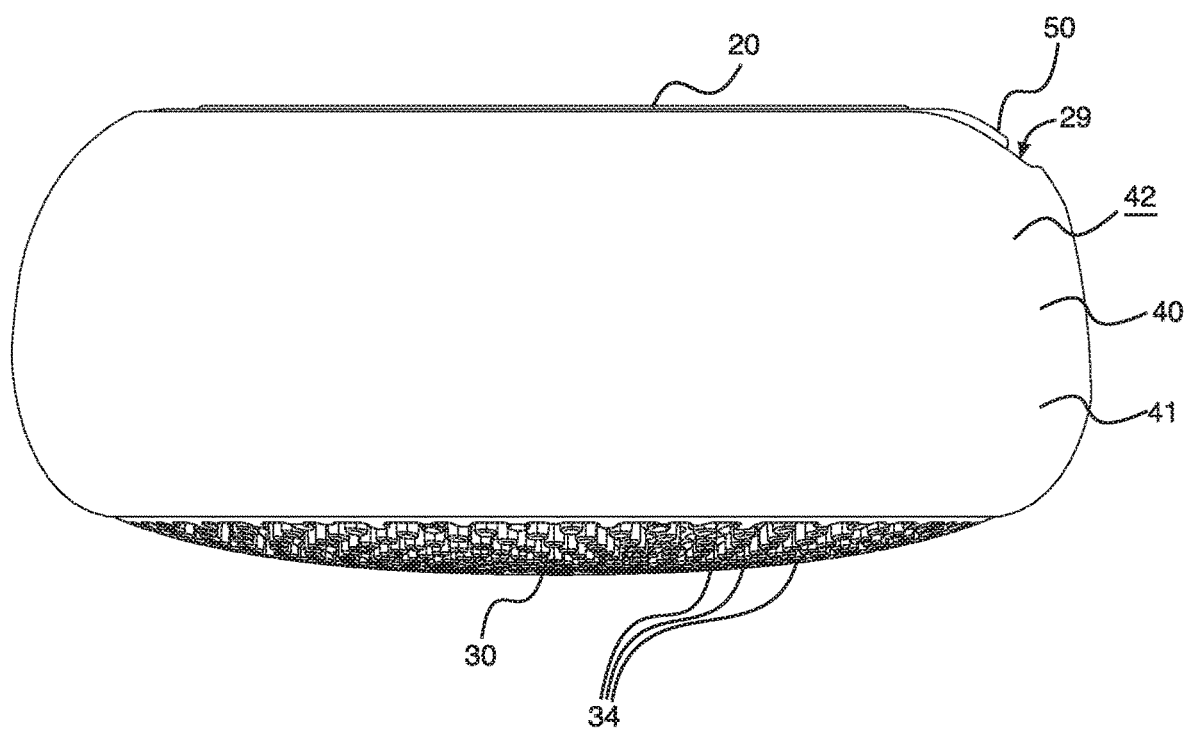
FIG. 7 is another side view of the skincare device illustrated in FIG. 1.
Figure 8:
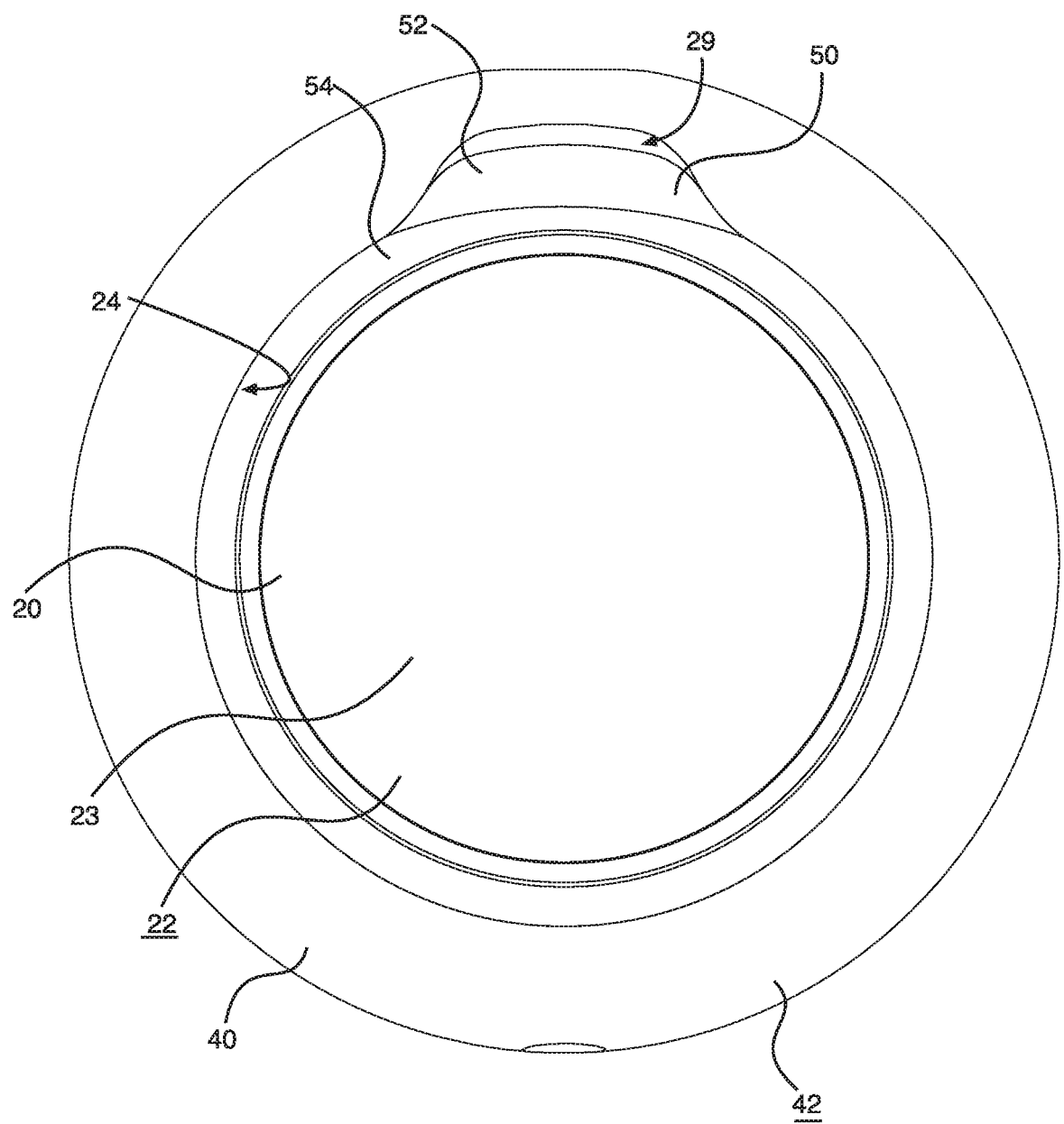
FIG. 8 is a top view of the skincare device illustrated in FIG. 1.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF SELECTED EXAMPLES

The following detailed description and the appended drawings describe and illustrate various skincare devices and methods of use. The description and drawings are provided to enable one skilled in the art to make and use one or more example skincare devices. They are not intended to limit the scope of the claims in any manner.

As used herein, the terms "heat therapy" and "heating therapy" refer to providing therapy to a user's skin via said skin's contact with a portion of a skincare device having a temperature that is above room temperature due to the functionality of said skincare device.

As used herein, the terms "cool therapy" and "cooling therapy" refer to providing therapy to a user's skin via said skin's contact with a portion of a skincare device having a temperature that is below room temperature due to the functionality of said skincare device and/or is lower in temperature than the same portion of the skincare device when that portion provides heat/heating therapy.

FIGS. 1, 2, 3, 3A, 4, 5, 6, 7, 8, and 9 illustrate an example skincare device 2. The skincare device 2 comprises a main body 10 that includes a number of components (described below). The main body 10 includes at least a first side 20, a second side 30, an intermediate portion 40 extending from the first side 20 to the second side 30, and a support member 14. It also includes a light source 100, a motor 80, and a temperature control unit 110, among other components.

The first side 20 is comprised of at least a portion of a panel 62 (described in greater detail below). More specifically, it is comprised of an upper portion 66 of the panel 62 designed to contact or be adjacent the face of a user. The upper portion 66 may contact the user directly or indirectly in order to provide treatment to the user. It is understood, thus, that references to the first side 20 necessarily reference the panel 62. In the illustrated embodiment, the panel 62 is comprised of a suitable material and provides at least some structural support for the skincare device 2 and its various components. The surface of the upper portion 66 is comprised of metal in this embodiment; consequently, the first side 20 is comprised, at least in part, of a metal in this embodiment. The first side 20 also defines a surface 22, which is substantially circular in shape and is defined by the upper portion 66 of the panel 62. The surface 22 provides heat and/or cool therapy to a user when the skincare device 2 is in use. It can also transmit vibrational therapy to a user.

The second side 30 is comprised of at least a portion of a temperature exchange component 112 (described in greater detail below). More specifically, it is comprised of a portion of the temperature exchange component 112 designed to be contacted by a user. It is understood, thus, that references to the second side 30 necessarily reference the temperature exchange component 112. In the illustrated embodiment, the temperature exchange component 112 defines a surface 32 that is comprised of a suitable metal. The temperature exchange component 112 provides structural support for the skincare device 2 and its various components, as well. As such, the second side 30 is comprised, at least in part, of a metal in this embodiment. The portion of the temperature exchange component 112 that does not comprise the surface 32 may be comprised of plastic or any other suitable material. The portion comprised of plastic may include its proximal end 31, which is disposed substantially opposite the surface 32. The proximal end 31 can attach to or connect with the support member 14 and be secured to the same, as described below.

The intermediate portion 40 is comprised of an annular member 41, which is disposed between and adjacent the first side 20 and the second side 30. More specifically, the intermediate portion 40 is comprised of a portion of the annular member 41 designed to be held by a user when the skincare device 2 is in use. In such instances, the first side 20 (or, in some embodiments, the second side 30) is adjacent to or in contact with a user's skin while the annular member 41 is held by a user. It is understood, thus, that references to the intermediate portion 40 reference the annular member 41. In the illustrated embodiment, the annular member 41 is disposed adjacent the first side 20 and the second side 30 and comprised of a material that may directly contact the skin. In this embodiment, the surface 42 of the annular member 41 (and, thus, intermediate portion 40) that will contact a user is comprised of silicone and disposed adjacent and in contact with the support member 14. In various embodiments, the annular member may be attached to the support member via an adhesive or one or more mechanical attachments. In some embodiments, the silicone may be medical-grade and/or a specially formulated, ultra-hygienic silicone. In different embodiments, the annular member may have any suitable shape and, in fact, may not be annular.

The main body 100 also includes a support member 14 having a proximal end 15 and a distal end 16, the distal end 16 being disposed nearer the temperature exchange component 112 than is the proximal end 15. The support member 14 is substantially disc-shaped and may be comprised of any suitable material, including plastic. The support member 14 is configured to attach and/or connect with the proximal end 31 of the temperature exchange component 112 and contact the annular member 41. The support member 14 and temperature exchange component 112 cooperatively provide a support to the various components disposed within the skincare device 2 and aid in giving the skincare device 2 its shape. In various embodiments, the support member may attach to or connect with the temperature exchange component via a snap-fit structure, an adhesive, or a mechanical attachment. The support member and temperature exchange component also may cooperatively define a passageway through which a portion of the controller may pass in some embodiments. One or both of the temperature exchange component and/or support member may attach to or connect with one or both of the frame and/or panel in other embodiments, as well.

A skilled artisan will be able to select suitable shapes, sizes, and materials for the various portions of the main body and skincare device according to a particular example based on various considerations, including the desired functionality of the device and the portion of the body the device is designed to treat. In one example, the entire main body and/or various portions thereof may be comprised of plastic, aluminum, silicone, and/or any other suitable material(s). In another example one or more of the first side, second side, and/or intermediate portion may have any suitable shape, including ring, sphere, circle, square, rectangle, cylinder, cone, and pyramid. In another embodiment, the first side may be comprised of any suitable material, including aluminum, an aluminum alloy, a zinc alloy, stainless steel, copper, ceramic, and other materials configured for thermal conduction. In a different embodiment, the second side may be comprised of any of suitable material, including aluminum, a zinc alloy, an aluminum alloy, stainless steel, copper, ceramic, and other materials configured for thermal conduction. In other embodiments, the intermediate portion may be comprised of any suitable material, including silicone compounds, plastic, rubber, and other similar materials. In various embodiments, the annular member may be comprised of any suitable material, including plastic and/or metal. The first side, the second side, the intermediate portion, and the annular member may have any suitable shape, as well. Furthermore, the annular member or the relevant portion of the temperature exchange component may be disposed at any position on the skincare device, including adjacent one or more of the first side, second side, or the intermediate portion in various embodiments. The portions of the skincare device may have varying sizes in different embodiments, as well. For example, in various embodiments the first side may have a diameter between about 2 centimeters ("cm") and about 20 cm, between about 4 cm and about 15 cm, and between about 6 cm and about 10 cm. In other embodiments the second side may have a diameter between about 2 cm and about 20 cm, between about 4 cm and about 15 cm, and between about 6 cm and about 10 cm. In different embodiments, the intermediate portion may have a height (which extends from the first side to the second side) between about 2 cm and about 20 cm, between about 4 cm and about 15 cm, and between about 6 cm and about 10 cm.

The first side 20 and the intermediate portion 40 cooperatively define a groove 24 that extends toward the second side 30. The groove 24 is adjacent the proximal end 15 of the support member 14. The groove 24 surrounds a flat, interior portion 23 of the first side 20 and is defined at its base by the annular member 41 and frame 82. The groove 24 includes an upper opening 26 adjacent the surface 22. The upper opening 26 is substantially circular in the illustrated embodiment. Accordingly, the groove 24 defined by the first side 20 is substantially annular, though it does abut a cutout 29 cooperatively defined by the first side 20 and the intermediate portion 40 which extends away from the interior portion 23. The groove 24 is configured to house and lock into place a locking mechanism 50 within the groove 24. Additionally, the groove 24 is disposed such that a light source 100 disposed distal to the surface 22 is able to emit light into and through the groove 24. A skilled artisan will be able to determine how to suitably configure the groove according to a particular example based on various considerations, including the desired shapes and sizes of the groove and locking mechanism and whether a light source is included in the device. In other embodiments, the groove and/or its opening may be triangular, square, rectangular, pentagonal, or have any other shape. In other embodiments, one or both of the first side and intermediate portion may, alone or in cooperation with one another, form zero, one two, three or more than three grooves. In various embodiments the groove may have a diameter between about 0.1 cm and about 5 cm, between about 0.5 cm and about 4 cm, and between about 1 cm and about 3 cm. In different embodiments, the groove may have a height between about 0.1 cm and about 5 cm, between about 0.5 cm and about 4 cm, and between about 1 cm and about 3 cm.

The light source 100 is disposed within a cavity 12 (described below) defined by the main body 10; specifically, it is attached to the controller 70 (described in greater detail below) and comprises of a number of lights 102 (including individual lights 102a, 102b, 102c, 102d). Each of the lights 102 extends from the controller 70 towards the first side 20. The light source 100 is disposed adjacent the groove 24 and beneath the surface 22 such that, when activated, the lights 102 of the light source 100 emit light into the groove 24 and onto any material or body part adjacent the first side 20. In the illustrated embodiment, the light source 100 comprises a number of light-emitting diode lights (hereinafter, "LED lights") that are configured to emit one or more of blue light, red light, and/or green light. As noted above, the emission of these various types of light onto human skin has known benefits. Blue LED light, for example, is known to aid in the destruction of bacteria. Red LED light is known to improve skin texture and tone, stimulate collagen, and accelerate the healing of the skin. Green LED light is known to help reduce skin discoloration and tighten the skin. These and other lights have other known benefits, as well. A skilled artisan will be able to select a suitable light source for a particular skincare device according to a particular example based on various considerations, including the size and shape of the device and the type(s) of light to be emitted by the light source. In another example, the light source may only emit one or more of blue, red, or green light. In an alternative example, the light source may also emit one or more of white, black, yellow, purple, pink, cyan, and orange light. In other embodiments, the light source may be comprised of any type of light, rather than an LED light. In various embodiments, the light source may comprise one, two, three, four, five, six, seven, eight, or more than eight individual lights. In different embodiments, the light source may be attached to the controller or any other component via a physical attachment or an adhesive; alternatively, various lights may be disposed on multiple other components via any suitable mechanism. In some embodiments, an individual light may only emit a single color; in other embodiments, an individual light may emit one, two, three, four, or more than four colors. Additionally, the lights may have different shapes in different embodiments, including box, cylinder, pyramid, sphere, and other suitable shapes.

As noted above, the locking mechanism 50 is configured to be inserted into and housed within the groove 24. The locking mechanism 50 is substantially annular and is substantially transparent such that light emitted by the light source 100 travels through the locking mechanism 50 relatively unhindered and onto a material or a user adjacent the first side 20. When the locking mechanism 50 is disposed within the groove 24, its first side 54 is disposed closer to the surface 22 than is its opposite, second side 56, which is disposed nearer the base of the groove 24.

The locking mechanism 50 is specifically configured to be repeatedly inserted into and removed from the groove 24; accordingly, it can be inserted and removed from the groove 24 as frequently as a user of the skincare device 2 sees fit. The locking mechanism 50 does not require the assistance of a further mechanism or device in order to be securely housed within the groove 24. Additionally, the locking mechanism 50 includes an extension 52 extending away from its center configured to be disposed over the cutout 29 defined by the skincare device 2 when the locking mechanism 50 is placed within the groove 24. The extension 52 is disposed over the cutout 29 in order to allow a user to readily remove the locking mechanism 50 from the skincare device 2 by grasping the extension 52. The locking mechanism 50 is also configured such that when a beauty accessory (described below) is inserted within the groove 24, the locking mechanism 50 may still be securely inserted into the groove 24 over a portion of the beauty accessory and hold the beauty accessory in place. A skilled artisan will be able to select a suitable a locking mechanism according to a particular example based on various considerations, including the shape and size of the groove and the beauty accessory to be locked into place. In other embodiments, the locking mechanism may be comprised of any material, including plastic, silicone or any other transparent, firm material. In different embodiments, the locking mechanism may not include an extension or may include two, three, or more than three extensions. In various other embodiments, the locking mechanism may have any shape, including conical, cylindrical, pyramidal, triangular, rectangular, and square. In alternative embodiments, an adhesive or mechanical component may be used to secure the locking mechanism within the skincare device.

The surface 32 of the second side 30 defines a set of protrusions 34 which extend away from the surface 32. Each protrusion of the set of protrusions 34 is integrally formed with the second side 30 (and, thus, the temperature exchange component) in the illustrated embodiment. Each protrusion of the set of protrusions 34 is comprised of the same material as the surface 32 in the illustrated embodiment, as well. However, in other embodiments, the set of protrusions may be attached to the second side via any mechanical attachment and/or via the use of an adhesive. Alternatively, some protrusions of the set of protrusions may be integrally formed with the second side and others may be attached to the second side in other embodiments.

Each protrusion of the set of protrusions 34 includes an upper surface 34a having a diameter. In the illustrated embodiment, the diameters of the various upper surfaces 34a are not uniform. Generally, the upper surfaces 34a of the protrusions of the set of protrusions 34 nearer the center portion 36 of the surface 32 of the second side 30 have smaller diameters than do the upper surfaces 34a of the protrusions of the set of protrusions 34 further from the center portion 36 and nearer to the lower portion 46 of the intermediate portion 40. Additionally, the center portion 36 of the second side 30 does not include protrusions. The protrusions of the set of protrusions 34 help to increase the surface area of the second side 30, which allows the skincare device 2 to more efficiently and quickly transfer heat away from the skincare device 2 as needed. In various embodiments, however, the set of protrusions may be comprised of any material and may have any alignment. A skilled artisan will be able to select suitable protrusion material(s) and alignments according to a particular example based on various considerations, including the size and shape of the second side and the desired functionality of the device. In various embodiments, the protrusions and/or surface of the second side may be comprised of any suitable metal, including a zinc alloy, an aluminum alloy, stainless steel, copper, ceramic, and other materials configured for thermal conduction. In other embodiments, the protrusions may be coated with gold, nickel, platinum, and/or another similar material. In different embodiments, some protrusions may be comprised of a first material, while other protrusions are comprised of a second material. In various other embodiments, any portion of the second side may include protrusions, including between about 5% and about 90% of the surface of the second side, between about 25% and about 70% of the surface of the second side, and between about 40% and about 55% of the surface of the second side. Additionally, in another embodiment, the center may include protrusions or, if it does not include protrusions, may include a logo or symbol. In various embodiments, one or more protrusion of the set of protrusions may have a height between about 0.1 millimeters ("mm") and about 6 cm, a height between about 2 mm and about 3 cm, and a height between about 5 mm and about 1 cm. In various embodiments, one or more protrusion of the set of protrusions may have a diameter between about 0.01 mm and about 5 cm, a diameter between about 0.1 mm and about 2.5 cm, and a diameter between about 0.5 mm and about 1 cm. In another embodiment, each protrusion of the set of protrusions may be comprised of silicone, which may additionally comprise all or part of the second side. In other embodiments, the second surface may define ridges, waves, pyramidal protrusions, elliptical protrusions, and other suitable components.

Figure 9:
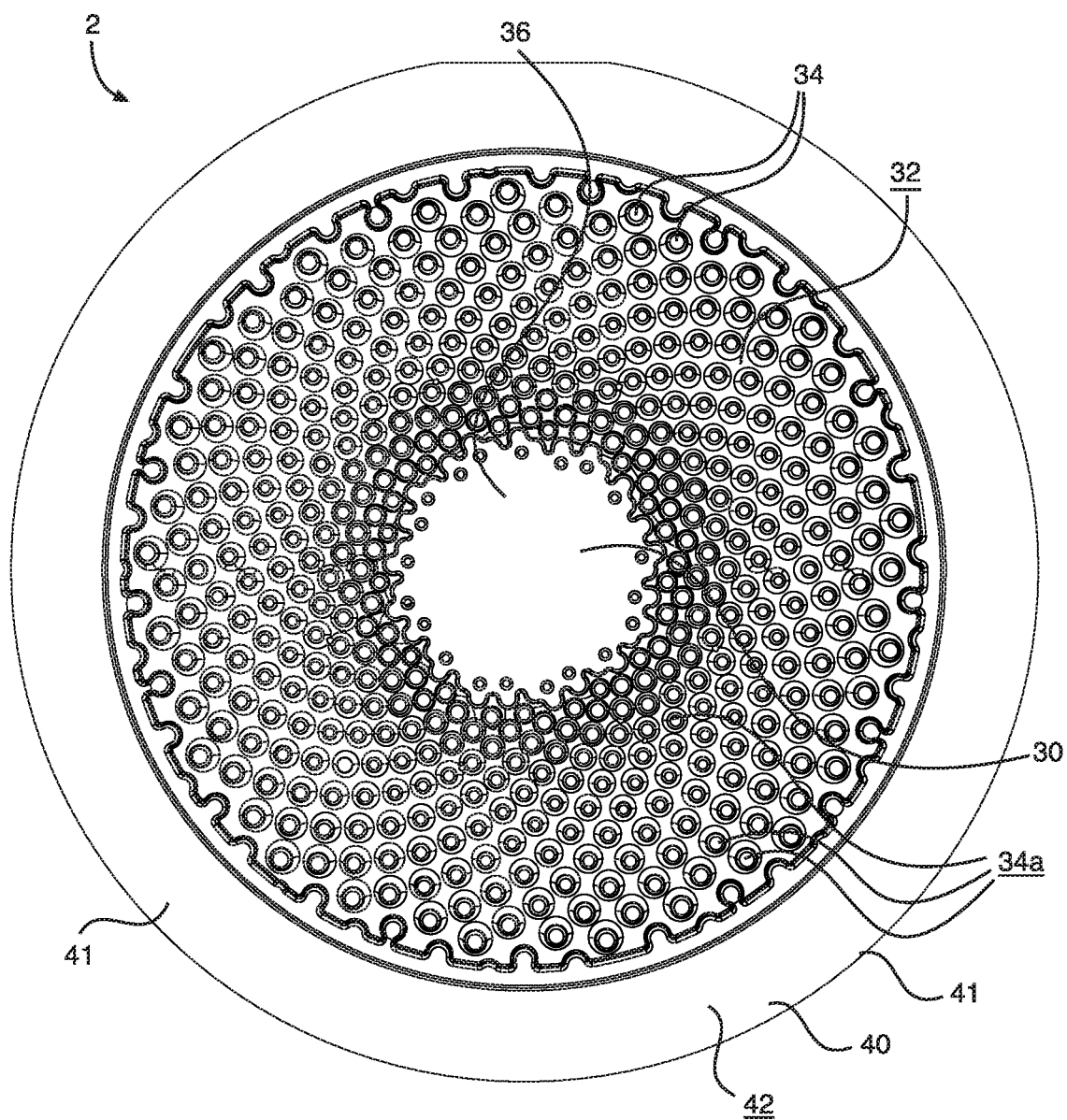
FIG. 9 is a bottom view of the skincare device illustrated in FIG. 1.
Figure 9A:
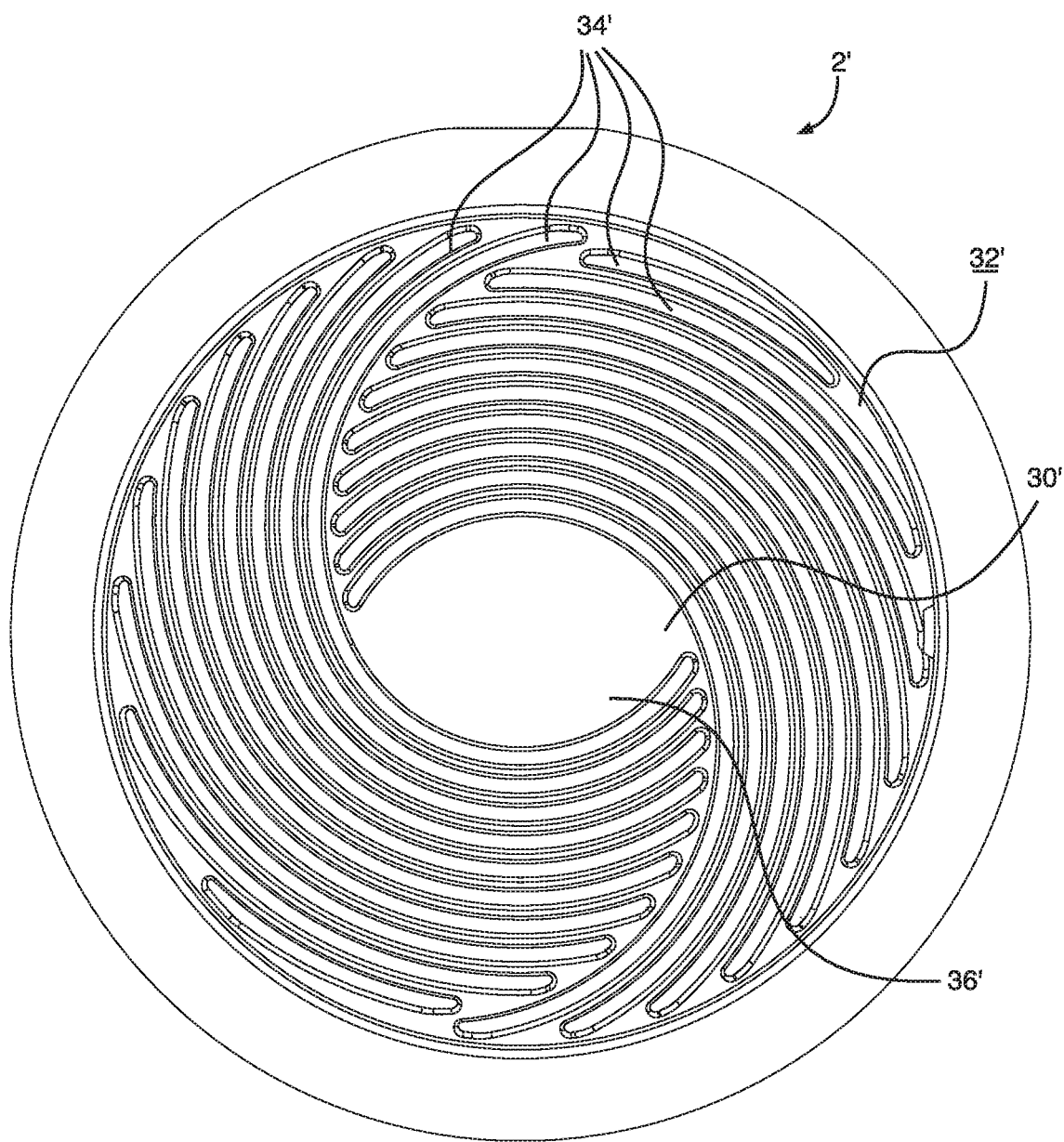
FIG. 9A is a bottom view of an alternative skincare device.

In an alternative skincare device 2', illustrated in FIG. 9A, the surface 32' of the second side 30' includes a set of waves 34' of varying length which extend away from the surface 32'. The waves of the set of waves 34' are comprised of metal, such as a zinc alloy, and are configured to transfer heat from the second side 30' away from the first side (not illustrated in the Figures) quickly and efficiently as needed; the increased surface area provided by the set of waves 34' helps to do so. Alternatively, the waves of the set of waves 34' may be comprised of ceramic. The set of waves 34' is configured to ensure that a wave-free center 36' is formed in the middle of the second surface 32'. A logo or symbol may be placed on the center 36'. In the illustrated embodiment, the waves of the set of waves vary in length; however, in other embodiments, each wave may have the same length. The number of waves of the set of waves may also vary according to different embodiments. A skilled artisan will be able to select suitable wave materials and alignment according to a particular example based on various considerations, including the size and shape of the second side and the functionality of the device. In various embodiments, the waves may be comprised of a zinc alloy, aluminum, an aluminum alloy, copper, stainless steel, ceramic, or any other suitable material. In other embodiments, the waves may be coated with gold, nickel, copper, or any other suitable material. In different embodiments, some waves may be comprised of a first material, while other waves are comprised of a second material. In various other embodiments, any portion of the second side may include waves, including between about 5% and about 90% of the surface of the second side, between about 25% and about 70% of the surface of the second side, and between about 40% and about 55% of the surface of the second side. Additionally, in another embodiment, the center may include waves.

As noted above, the main body 10 defines a cavity 12 configured to house various components. The cavity 12 is cooperatively defined by the various components defining the first side 20, the second side 30, and the intermediate portion 40, including the panel 62, the temperature exchange component 112, frame 82, and support member 14.

One component housed within the cavity 12 of the main body 10 is a power source 60. The power source 60 is operatively connected to and provides power to the various components of the skincare device 2 (such as the light source 100 and others described below) so that they may function efficiently and properly. The power source 60 comprises a rechargeable lithium-ion battery in the illustrated embodiment and may be charged through a charging port, such as DC jack 68 best shown in FIG. 5. The power source 60 is housed within a panel 62 defining a slot 64 into which the battery 60 is stored. The panel 62 aids in conducting and/or removing heat from the temperature control unit (described below) to one or both of the first side 20 and second side 30. The panel 62 also secures the power source 60 in place within the skincare device 2. Additionally, the panel 62 includes an upper portion 66 which defines at least a portion of the first side 20, including the surface 22, as described above. A skilled artisan will be able to select a suitable power source and panel according to a particular example based on various considerations, including the various components housed within the skincare device and the desired dimensions of the skincare device. In other embodiments, the power source may comprise one, two, three, or more than three replaceable dry cell batteries. In different embodiments, the power source may comprise a lithium polymer battery or batteries. In various embodiments, the panel may be comprised of any suitable material(s), including aluminum, an aluminum alloy, a zinc alloy, copper, stainless steel, gold, silver, ceramic, and other suitable materials. In additional embodiments, the light source may emit one or more of red, blue, pink, and/or green light to show that the power source is successfully charging and/or holds a full charge; in one such example, the light source emits white light that rotates through the groove in a circular motion to show the device is charging and a solid purple light emitted from the device shows that the device is fully charged. In other embodiments, a portion of the panel may be coated with a thermal film or paste which helps to protect the power source from the heat generated by the skincare device when in use. In various embodiments, the upper portion and/or surface of the panel may have a diameter between about 2 cm and about 15 cm, between about 4 cm and about 12 cm, and between about 6 cm and about 9 cm.

The power source 60 provides power to the controller 70, which is also housed within cavity 12 defined by the main body 10. The controller 70 is operatively connected to each of the light source 100, motor 80, and temperature control unit 110 and provides instructions to and controls each of these components. The controller 70 is activated by the user control 72, which is disposed on the intermediate portion 40 and operatively connected to the controller 70. The controller 70 in the illustrated embodiment includes a printed circuit board assembly ("PCBA") and related circuitry; however, in other embodiments, the controller may comprise any device suitable to control the skincare device's components, such as a printed circuit board ("PCB") or any other suitable computer or mechanism for communicating information. Additionally, the controller 70 may be operatively connected to an interface 90, allowing it to communicate with a second device (described in greater detail, below).

The user control 72 comprises a button which, when pressed, activates the skincare device 2. Repeated and/or a specific type of use of the user control 72 allows for a user to cycle through various modes of operation of the skincare device 2 (described in greater detail, below). Potential vibration modes that may be activated by the user control 72, for example, may include low frequency mode, high frequency mode, stochastic mode, and alternating frequency mode. Additionally, various patterns of light emissions, heating patterns, and cooling patterns may be selected by the user via the user control 72. A skilled artisan will be able to suitably place the user control on the device and configure the same according to a particular example based on various considerations, including the number of desired modes and the materials comprising the main body. In other embodiments, the user control may be disposed on any side of the main body. In a different embodiment, the skincare device may comprise zero, two, three, or more than three user controls. In additional embodiments, the user control may include separate user controls configured to control individual components and/or actions.

The motor 80 is disposed within the main body 10 and is operatively connected to the power source 60 and the controller 70. The motor 80 is disposed within in a frame 82 within the main body 10. The frame 82 is configured to support the motor 80 and keep the motor 80 secured at a particular location inside the main body 10, as well as provide general structural support to the skincare device 2. Specifically, the frame 82 includes an arm 84 that defines a slot 86 into which the motor 80 is disposed. The arm 84 (and slot 86) extends away from the main body 83 of the frame 82 towards the second side 30 and allows the inner surface (not illustrated in the Figures) of the arm 84 to secure the motor 80 and hold it in place. The motor 80 is disposed substantially adjacent the first side 20 so its vibrations may be efficiently transmitted to the user via the first side 20. At least a portion of the frame 82, including its proximal end 88, is comprised of a substantially transparent plastic. Accordingly, the proximal end 88 of the frame 82 allows for light generated by the light source 100 to pass through the proximal end 88 and surface 89 of the frame 82 relatively unhindered.

The controller 70 provides instructions to the motor 80, which is powered by the power source 60. A high or low-frequency motor 80 may be used to create pulsations that vibrate the skincare device in various embodiments. The motor 80 in this embodiment is configured to produce a range of frequencies that may provide beneficial treatment of the skin. When the skincare device 2, and the first side 20 in particular, is applied to the body, such as the face or neck, the motor 80 provides vibrations to the skin. A skilled artisan will be able to select suitable motors, frames, and vibration ranges based on various considerations, including the size and shape of the skincare device and the desired vibration strength of the device. Examples of suitable ranges for vibration frequencies includes vibration frequencies between about 80 Hertz ("Hz") and about 200 Hz, vibration frequencies between about 100 Hz and about 180 Hz, and vibration frequencies between about 120 Hz and about 150 Hz. In another embodiment, the skincare device may include two or more motors. In another embodiment, a motor may be stochastic. In other embodiments, the frame may be omitted. In different embodiments, the frame may not include a slot or arm, but may instead house the device entirely within its main body. In some embodiments, there may be more than one motor; in embodiments containing multiple motors, the motors may vary from one another in frequency output.

The controller 70 also controls an interface 90 that is a component of the controller 70. The interface 90 allows the skincare device 2 to communicate with a second device, such as a personal computer, tablet, mobile telephone, or other electronic device (not illustrated in the Figures). Using the interface 90, the skincare device 2 can send information to other devices so that the other device(s) may collect data pertaining to the use of the skincare device 2. Additionally, the skincare device 2 may receive control signals from another device that can indicate that the skincare device 2 should turn on or off, increase or decrease speed, switch to a different vibration, lighting, heating or cooling pattern, and/or switch to a pre-set pattern desired by the user or recommended by the other device, among other instructions. The interface 90 can be a wired or a wireless interface, such as a wireless transceiver that transmits control signals between the skincare device 2 and the second device. A skilled artisan will be able to select a suitable interface based on various considerations, including the device with which the skincare device will communicate and the size and shape of the main body. In some embodiments, the interface is a radio-frequency ("RF") transceiver used to transmit and receive RF signals between the skincare device and other devices. One example of an RF transceiver that could be used is a low power 2.4 GHz RF transceiver. In various embodiments, the skincare device may also include antennas for transmitting and receiving signals between the skincare device and other devices. In such examples, the interface can use BLUETOOTH®, Wi-Fi, infrared, laser light, visible light, acoustic energy, or one of a number of other methods to transmit information wirelessly between the skincare device and another device. In another embodiment, the controller can specifically communicate with another device to confirm the skincare device's authenticity, as more fully described below and illustrated in FIG. 30.

Figure 10:
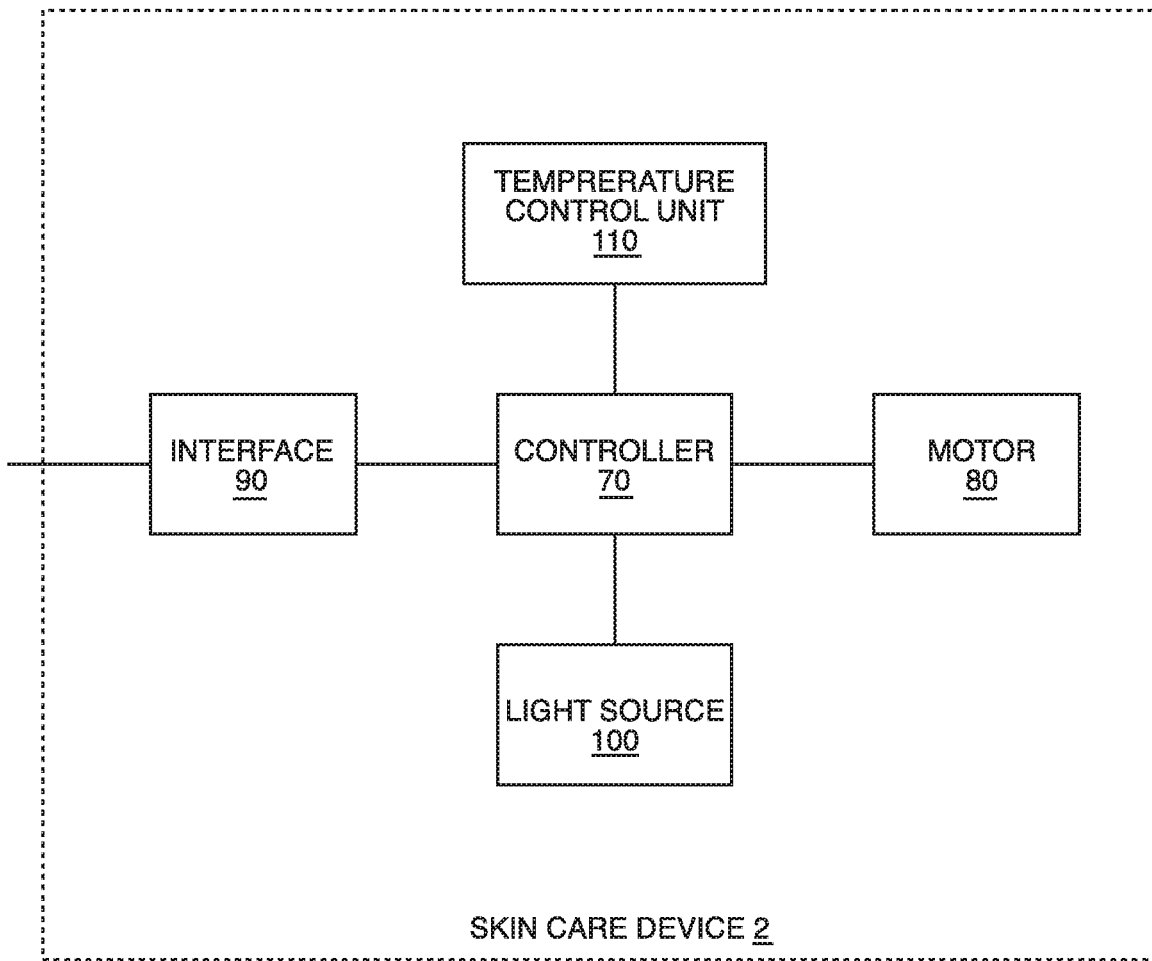
FIG. 10 is a diagram illustrating components of a networked skincare device in an example embodiment.

In some embodiments, the skincare device is connected to a network via the second device. In other embodiments, the skincare device is directly connected to a wireless router or cellular phone network and may connect with the second device in any of said manners. Accordingly, the skincare device can be controlled via personal computer, tablet, mobile phone, or other suitable electronic devices a user using the personal computer, tablet, phone, or other device. FIG. 10 illustrates one example of such a design.

FIG. 10 is a diagram illustrating components of a, networked skincare device, such as skincare device 2, in accordance with an example embodiment. In this embodiment, the skincare device includes a controller, such as controller 70, a motor, such as motor 80, a light source, such as light source 100, a temperature control unit, such as temperature control unit 110, and an interface, such as interface 90. As explained above, the skincare device can be connected to a network via a personal computer, tablet, mobile telephone, or other electronic device or can be directly connected to a wireless router or cellular phone network. Thus, the skincare device can be controlled by, transmit data to, and/or receive data from the personal computer, tablet, mobile telephone, or other electronic device via the aforementioned mechanisms. The interface may be wired or wireless and may include any of those described above. A skilled artisan will be able to determine how to suitably connect the skincare device with other devices based on various considerations, including the desirability of doing so and the devices to which connection would be beneficial. In some embodiments, the skincare device may not include an interface and, thus, may not communicate with other devices. In different embodiments, the skincare device may only transmit data to other devices; it may not receive any data and cannot be controlled via said other devices in this embodiment.

Example data that the skincare device may communicate to one or more of a personal computer, tablet, mobile telephone, or other electronic device may include the number of uses of the skincare device, the durations of the various uses of the skincare device, the user's preferred skincare device settings, and various other types of information related to the use of the device.

As noted above, the skincare device 2 also includes a temperature control unit 110, which is operatively connected to each of the power source 60 and the controller 70 in the illustrated embodiment. The temperature control unit 110, thus, receives power from the power source 60 and operation instructions from the controller 70. In various embodiments, any suitable material(s) and/or component(s) may comprise the temperature control unit. Examples of suitable materials that may comprise the temperature control unit include copper alloy(s), polyimide(s), ceramic, and other suitable materials. The temperature control unit may comprise a positive temperature coefficient thermistor in some embodiments.

The temperature control unit 110 is substantially box-shaped and is disposed adjacent a temperature exchange component 112 within the cavity 12 of the main body 10. The temperature exchange component 112 helps to secure the temperature control unit 110 in a desired position within the skincare device 2. The temperature control unit 110 is also disposed sufficiently adjacent the first side 20 such that its heat absorption and/or release may easily flow towards and/or away from the upper portion 66 of the panel 62. In the illustrated embodiment, the temperature exchange component 112 can act as a heatsink that is configured to aid in preventing the skincare device 2 from overheating; in other embodiments, however, any suitable unit or component may comprise the temperature exchange component. A skilled artisan will be able to select a suitable temperature control unit and a suitable temperature exchange component according to a particular example based on various considerations, including the materials comprising the first and second sides of the main body and the desired functionality of the skincare device. In different embodiments, one or more heatsinks can be used along with the temperature exchange component. In alternate embodiments, the temperature exchange component may be comprised of any suitable material, including copper, copper alloys, aluminum, diamond, stainless steel, ceramic, and other suitable materials. In various other embodiments, each of the temperature control unit and temperature exchange component and its various parts may have any suitable shape, including sphere, box, ovoid, pyramid, circular, triangular, rectangular, and/or round. In various embodiments, the temperature exchange component may be comprised of one or more of an aluminum alloy, a ceramic, stainless steel, and/or other suitable materials.

The temperature control unit 110 is configured such that it is capable of absorbing heat from and/or releasing heat toward the first side 20 and second side 30 of the skincare device 2 after instruction by the controller 70. The temperature control unit 110 includes different types of conductors, which allows it to absorb and/or release heat on each end of the device, as instructed by the controller 70 based on the various electric signals sent and/or electric field generated by the various components of the skincare device 2. This allows the portions of the temperature control unit nearer the first end 20 and second end 30 to absorb and/or release heat as per the controller's 70 instruction based on the direction of the current provided by the various components of the skincare device 2.

In operation, the power source 60 and controller 70 provides current, power, and direction to the temperature control unit 110 via circuitry connecting the power source 60, the controller 70, and the temperature control unit 110. Once the instructions and power are received, the temperature control 110 unit can absorb heat from its distal end 109 and release it towards the first side 20 via its proximal end 108, which allows the first side 20 to be heated relative to when the skincare device 2 is not in operation. Such a release provides heat therapy to a user. The temperature control unit 110 can also absorb heat via its proximal end 108 and transfer it away from the first side 20 via its distal end 109 and, specifically, via the temperature exchange component 112. This allows the first side 20 to be cooled relative to when the skincare device 2 is not in operation (or, in some embodiments, when heat is released through the first end to provide heat therapy). Doing so provides cool therapy to a user.

In greater detail, when a user desires heat therapy the temperature control unit 110 absorbs heat via its distal end 109 and releases said heat via its proximal end 108 toward the panel 62 to which it is adjacent, which then conducts and transfers the heat to the surface of the first side 20. Conversely, when a user desires cool therapy the temperature control unit 110 absorbs heat via its proximal end 108 and releases said heat via its distal end 109 toward the temperature exchange component 112 to which it is adjacent. This transfers heat away the first side 20, cooling it relative to when the skincare device 2 is not in use (and/or is providing heat therapy). In either instance, the first side 20 may be contacted by a user either directly or indirectly via the use of a beauty accessory as an intermediary between the skin and the skincare device 2.

In various embodiments, the temperature control unit may heat the surface of the first side to temperatures between about 70 degrees Fahrenheit ("° F.") and about 150° F., between about 75° F. and about 125° F., and between about 80° F. and about 100° F. In other embodiments, the temperature control unit may cool the surface of the first side to temperatures between about 30° F. and about 80° F., between about 40° F. and about 70° F., and between about 50° F. and about 60° F. In an alternative embodiment, the temperature control unit may be in direct contact with or directly adjacent the first side and/or panel. In some embodiments, the temperature control unit may include one or both of an N-type semiconductor and a P-type semiconductor, which may comprise the mechanism through which heat is absorbed and/or released by the proximal and distal ends of the temperature control unit.

The temperature exchange component 112 is configured to safely and properly dispose of excess heat generated by the temperature control unit 110 when the skincare device 2 provides heating and cooling therapy. One way it can do so is by transferring the heat generated by the temperature control unit 110 to the surface 32 of the second side 30, which, as stated above, includes a portion of the temperature exchange component 112. As previously stated, the set of protrusions 34 of the second side 30 provide additional surface area (relative to a flat surface) to more quickly and efficiently transfer said heat away from the first side 20 in the form of air or a fluid. This can be done when providing cooling therapy, for example.

A skilled artisan will be able to select a suitable temperature control unit according to a particular example based on various considerations, including the side of the device to which heating or cooling therapy is desired and the shape and size of the device. In other embodiments, the temperature control unit may be configured to heat the second side of the main body for use on human skin, rather than the first side. In a different embodiment, the temperature control unit may transfer heat away from the main body via its first side, rather than the second side. In various other embodiments, the temperature control unit may disperse heat to the intermediate portion.

In an alternative embodiment, the skincare device may only cool the first side of the skincare device and only heat the second side of the skincare device. In such an embodiment, both sides of the device may be configured to provide therapy to human skin directly or indirectly. Additionally, in another embodiment, first side may be heated and the second side may be cooled. In another alternative, the temperature control unit may heat and cool the first side and/or may heat and cool the second side, depending on the mode the skincare device is in and the instructions the temperature control unit receives from the controller. In another embodiment, the temperature control unit may simply emit heat in one or several directions; it may not be capable of cooling a side in such an embodiment.

A first temperature sensor 120 and a second temperature sensor 122 (collectively, the "sensors 120, 122") are also disposed within the main body 10. The sensors 120, 122 are substantially pill-shaped and include tails 120a, 122a, respectively. The sensors 120, 122 are operatively connected to each of the power source 60 and controller 70 and are configured to measure the temperature of the skincare device 2 and report said temperature to the controller 70. If one of the sensors 120, 122 detects that the temperature of the skincare device 2 passes a certain threshold, it will transmit said information to the controller 70 and the controller 70 will initiate a "shut down" of the device in order to protect its user from the potential effects of an overheated device (such as burning the skin, for example). In such instances, the skincare device 2 will cease operating; such a cessation of operation may be permanent or temporary. Two sensors 120, 122 are included to ensure that, in the event that the first sensor 120 or the second sensor 122 malfunctions, the skincare device 2 will still have a working sensor to detect its temperature and shut down, if necessary. In the illustrated embodiment, each of the first and second sensors 120, 122 comprises a negative temperature coefficient thermistor; however, in other embodiments, the first and second sensors may be comprised of any suitable component. A skilled artisan will be able to select suitable first and second sensors according to a particular example based on various considerations, including the specific temperature control unit used and the size and shape of the device. In different embodiments, the sensors may be comprised of any suitable material, including various semiconductors, copper, and other suitable materials. In yet other embodiments, the skincare device may include zero, one, three, or more than three sensors. In various examples, one or both of the sensors may instruct the controller to cease operation of the device when the sensor detects a temperature that exceeds about 120° F., about 150° F., and about 180° F. Alternatively, a thermal fuse may be used in place of one or both of the sensors.

Figure 11A:
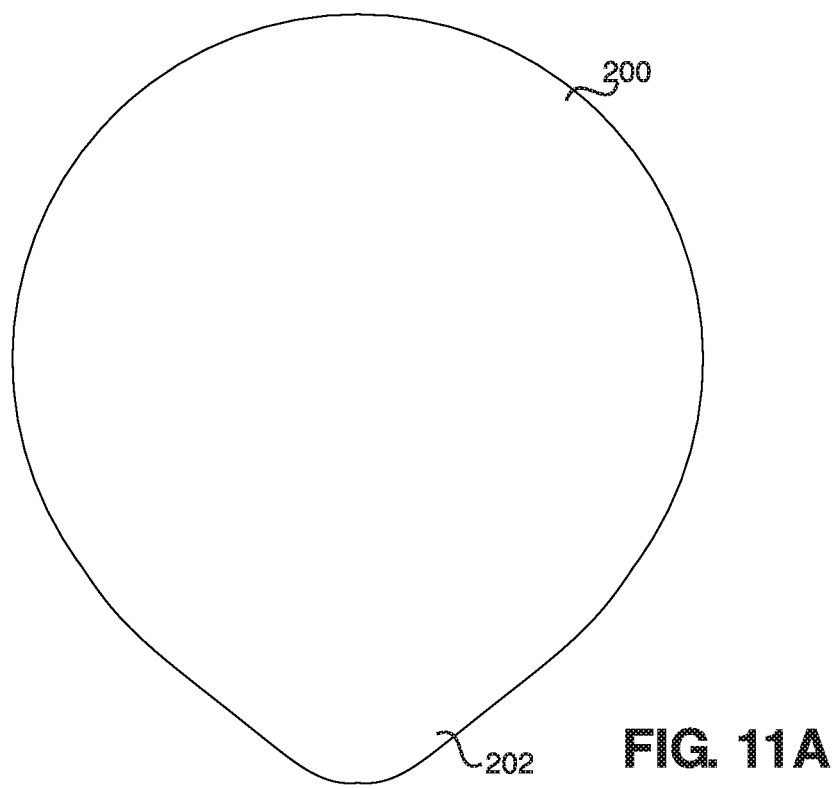
FIG. 11A is a top view of an example beauty accessory.
Figure 11B:
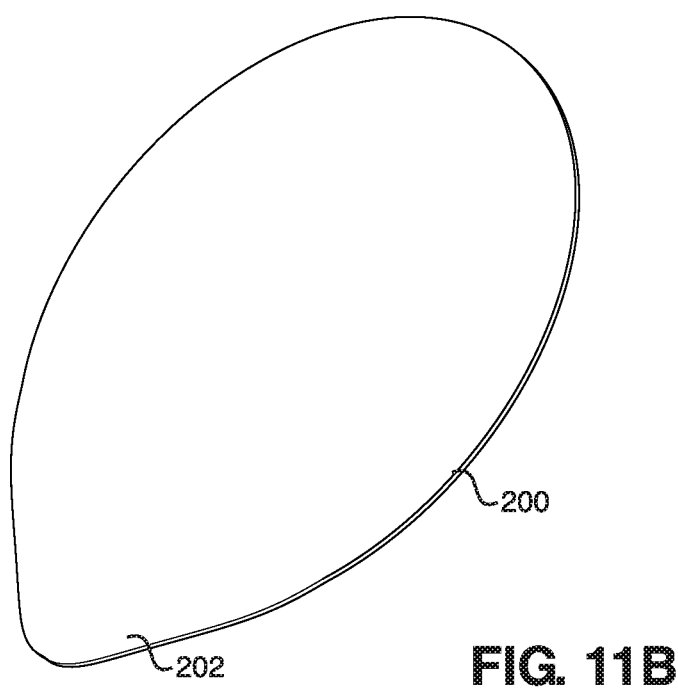
FIG. 11B is a perspective view of the beauty accessory illustrated in FIG. 11A.

Various beauty accessories may be used in conjunction with the skincare device 2. Example beauty accessories include one or more facial masks 200, best illustrated in FIGS. 11A and 11B. In other embodiments, however, other types of beauty accessories may be used. A facial mask, such as facial mask 200, is a cosmetic that is designed to be coated, filled, or layered with various serums, liquids, compounds, and similar items. Facial masks are known in the beauty industry, primarily in the form of masks which nearly cover the user's entire face. They are left on the user so that the materials and/or serums or cosmetics are in contact with the face for an extended period of time and may be absorbed by the user's skin. The illustrated facial mask 200, on the other hand, only contacts a portion of the user's face and it will only be in contact with the same for a short period of time; namely, when the skincare device 2 is in use.

The heating, cooling, vibrations, and/or light generated by the skincare device 2 help the contents of the facial mask 200 to be absorbed more quickly by the skin than are the contents of a traditional mask that is placed on the face for an extended period of time. In various examples, the facial mask may be comprised of cloth, mesh, various microfibers, silicone, a combination of one or more of these, and/or any other suitable material. In additional examples, the facial masks may be coated in, comprised of, include, or otherwise incorporate one or more the following materials and/or compounds, either alone or in combination: water, glycerin, butylene glycol, dipropylene clycol, caprylic/capric triglyceride, cetyl ethylhexanoate, diglycerin decyl cocoate, hydroxyacetophenone, panthenol, allantoin, cetearyl olivate, sorbitan olivate, tromethamine, caprylic/capric glycerides, niacinamide, carbomer, various acrylates, caprylyl glycol, dipotassium glycyrrhizate, tocopheryl acetate, ethylhexyglycerin, tremella fuciformis sporocarp exract, xanthan gum, simmondsia chinesis seed oil, frangrange, *Portulaca oleracea* extract, xylitylglucoside, anhydroxylitol, 3-o-ethyl ascorbic acid, glucose, 1,2-hexanediol, pearl extract, *Portulaca oleracea* extract, hydrogenated lecithin, ceramide 3, butylene glycol, decyl cocoate, glycereth-26, shea butter, PEG-100 stearate, polysorbate 60, tromethamine, carnosine, hydrolyzed collagen, palmitoyl tripeptide-5, and other suitable compounds.

The facial mask 200 is configured such that it can be placed on the surface 22 of the first side 20 and locked into place on the skincare device 2 through use of the locking mechanism 50, which is placed over the facial mask 200 once it is positioned on the skincare device 2. The facial mask 200 is relatively circular in shape and thin. The facial mask 200 also includes a protrusion 202 extending away from the body of the facial mask 200, which allows the user to easily grasp the facial mask 200. The locking mechanism 50 locks one facial mask 200 at a time in place by securing a portion of a facial mask 200 within the groove 24 and securing another portion of a mask 200 atop the interior portion 23 of the first side 20 when the locking mechanism 50 is secured to the skincare device 2.

Figure 12A:
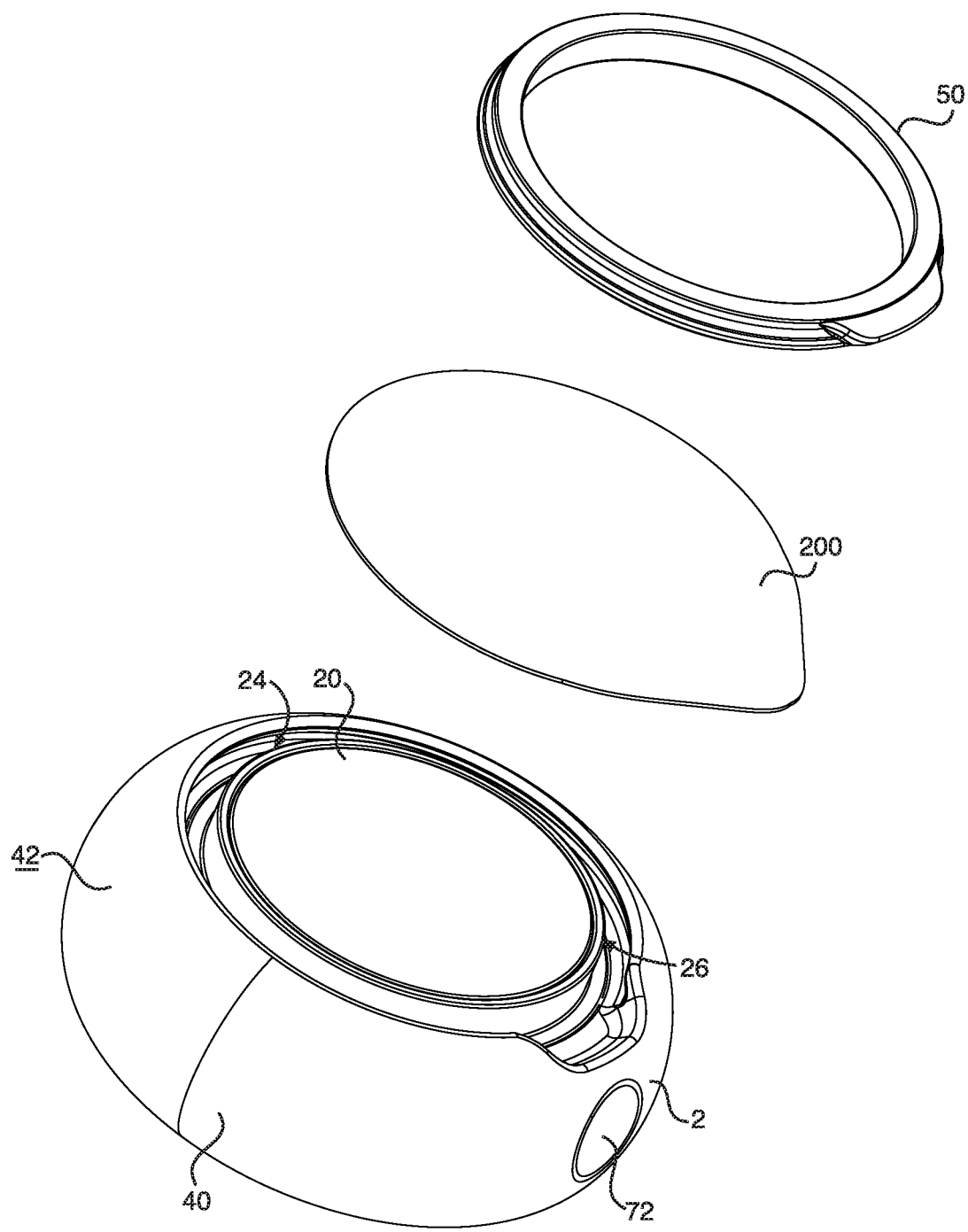
FIG. 12A is a perspective view of the beauty accessory illustrated in FIG. 11A and the skincare device illustrated in FIG. 1, with the locking mechanism of the skincare device removed and aligned with the beauty accessory over the first side of the skincare device.
Figure 12B:
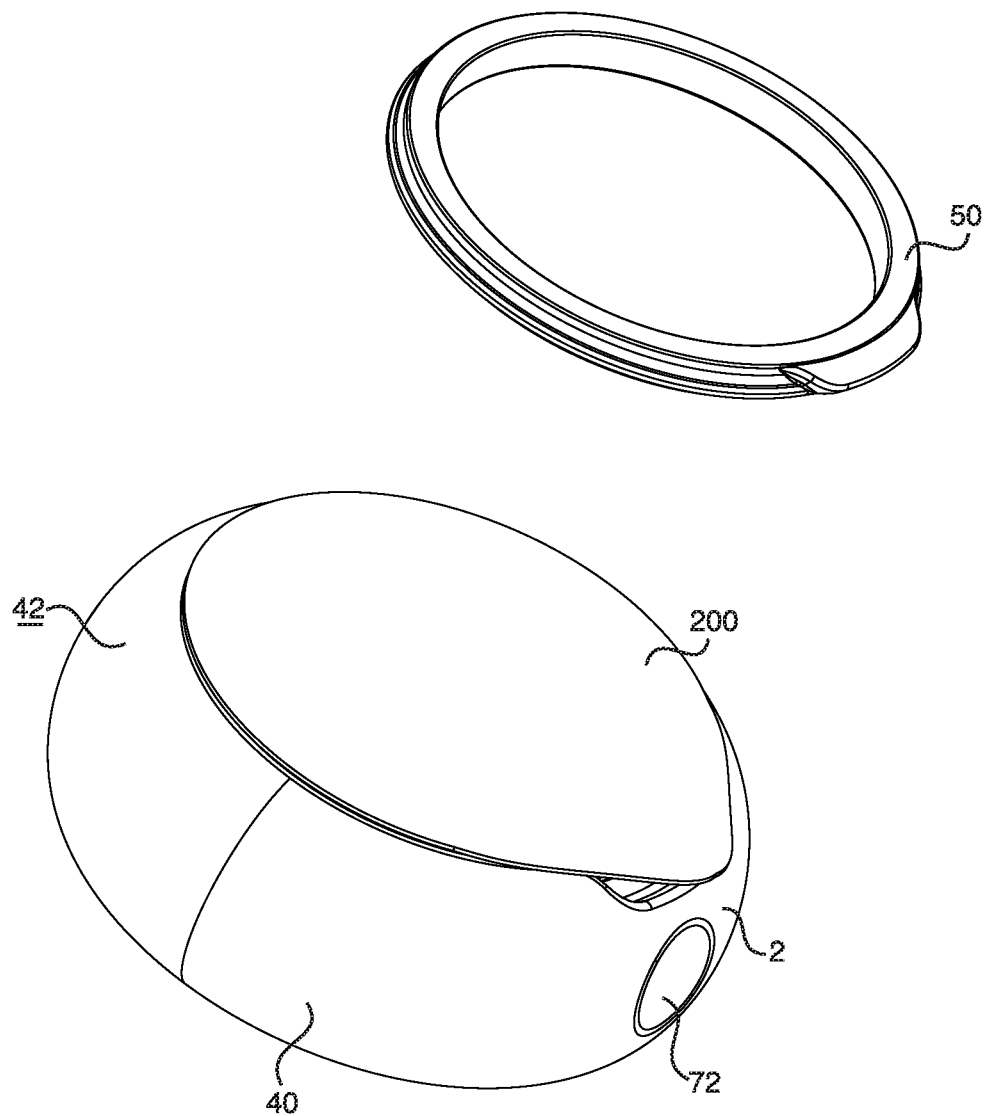
FIG. 12B is a perspective view of the beauty accessory and skincare device illustrated in FIG. 12A, with the beauty accessory placed in contact with the first side of the skincare device and the locking mechanism aligned with, but not in contact with, the first side of the skincare device.
Figure 12C:
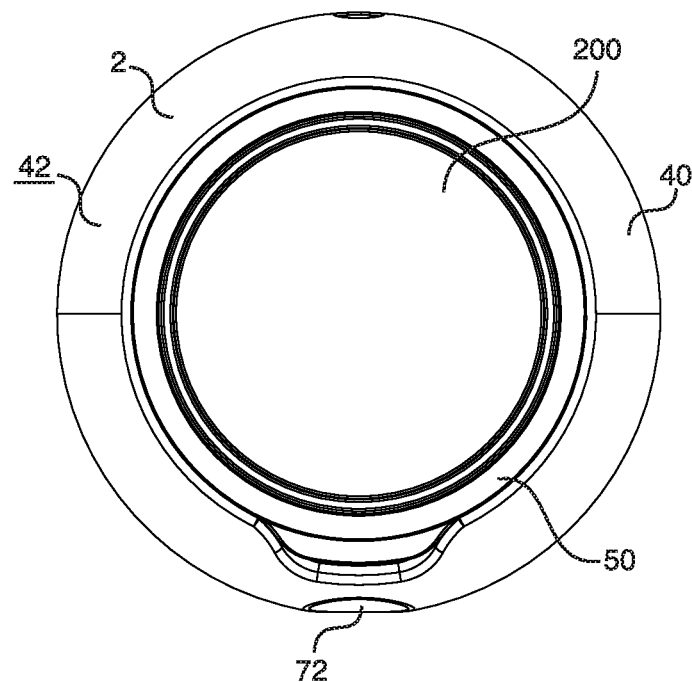
FIG. 12C is a top view of the beauty accessory and skincare device illustrated in FIG. 12A, with the facial mask secured to the first side of the skincare device via the locking mechanism.
Figure 12D:
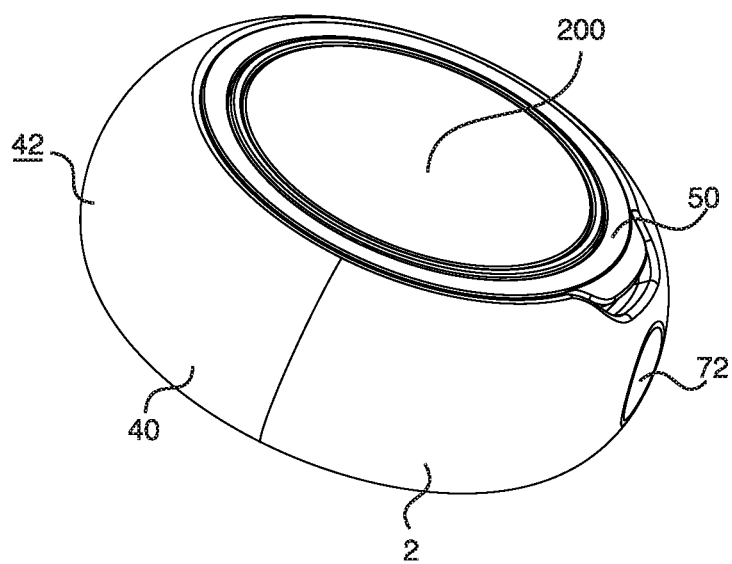
FIG. 12D is a perspective view of the beauty accessory and skincare device illustrated in FIG. 12C.
Figure 13:
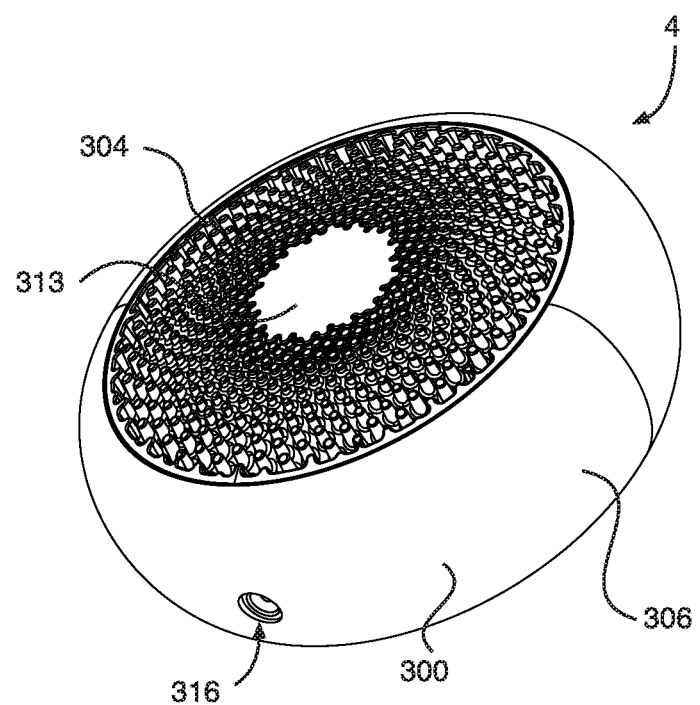
FIG. 13 is a perspective view of a second example skincare device.
Figure 14:
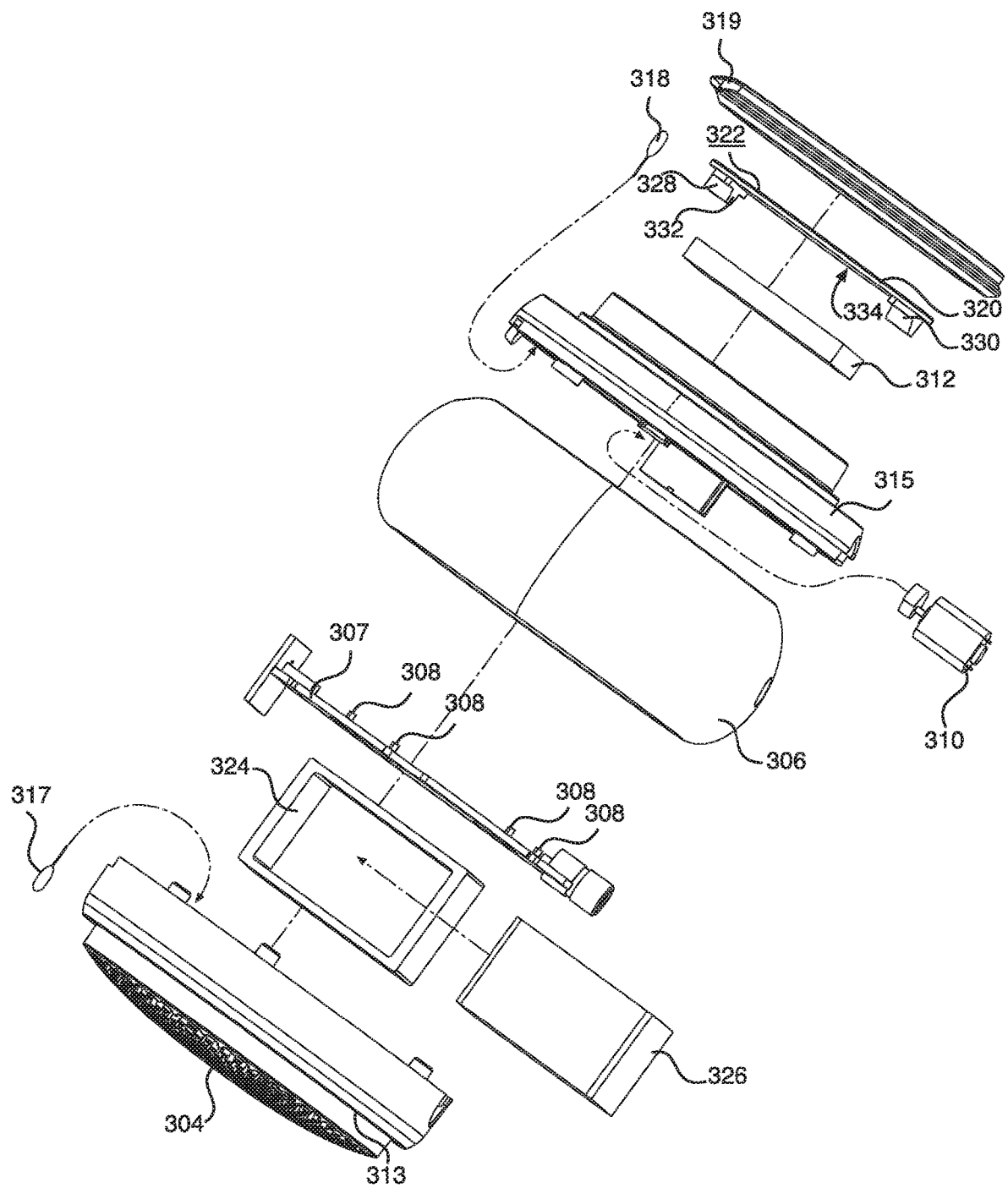
FIG. 14 is an exploded view of the skincare device illustrated in FIG. 13.
Figure 15:
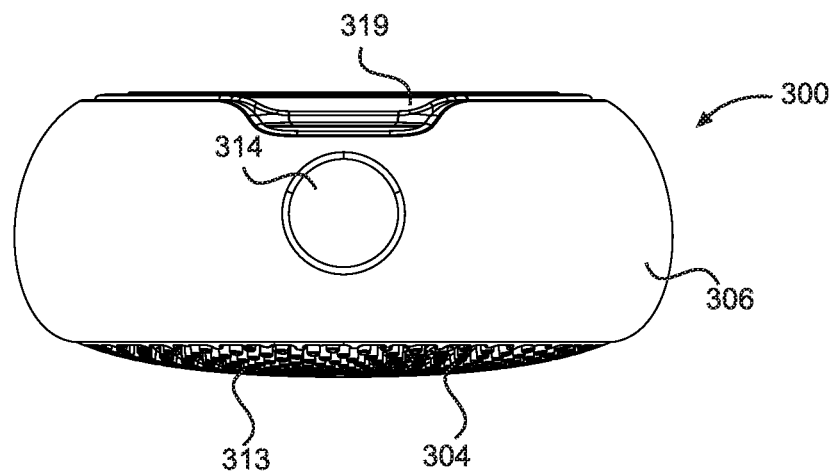
FIG. 15 is an end view of the skincare device illustrated in FIG. 13.
Figure 15A:
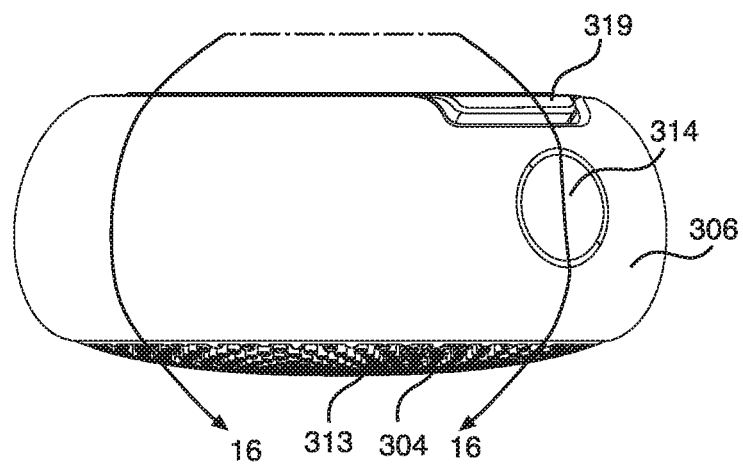
FIG. 15A is an end view of the skincare device illustrated in FIG. 13 in which the skincare device has been rotated slightly.
Figure 16:
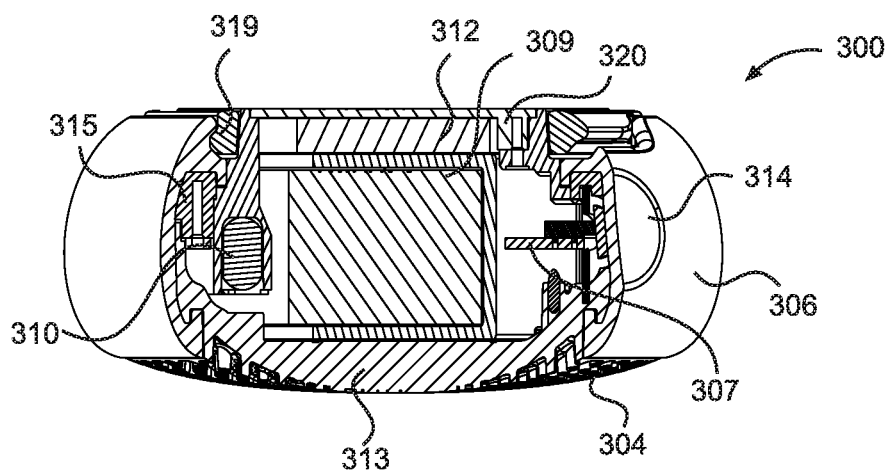
FIG. 16 is a sectional view of the skincare device illustrated in FIG. 15A, taken along line 16-16.
Figure 17:
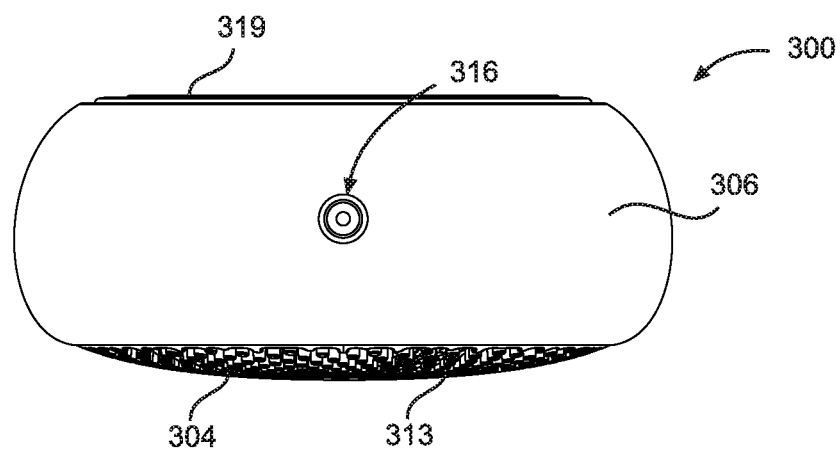
FIG. 17 is another end view of the skincare device illustrated in FIG. 13.
Figure 18:
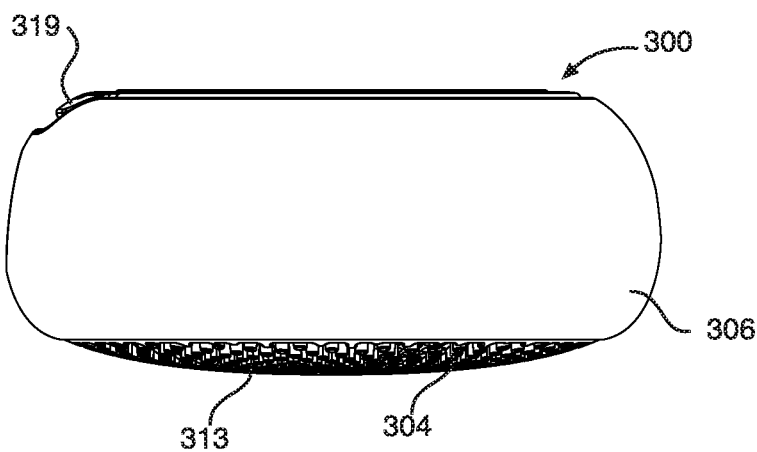
FIG. 18 is a side view of the skincare device illustrated in FIG. 13.
Figure 19:
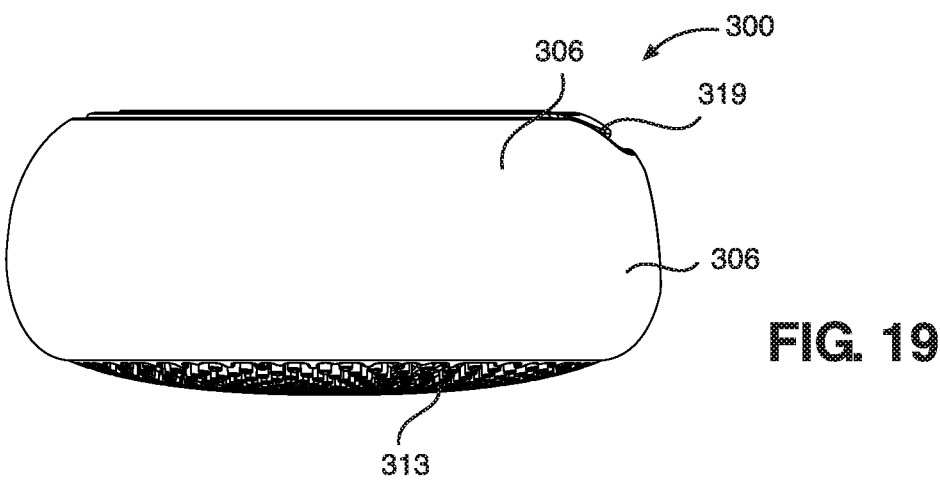
FIG. 19 is another side view of the skincare device illustrated in FIG. 13.
Figure 20:
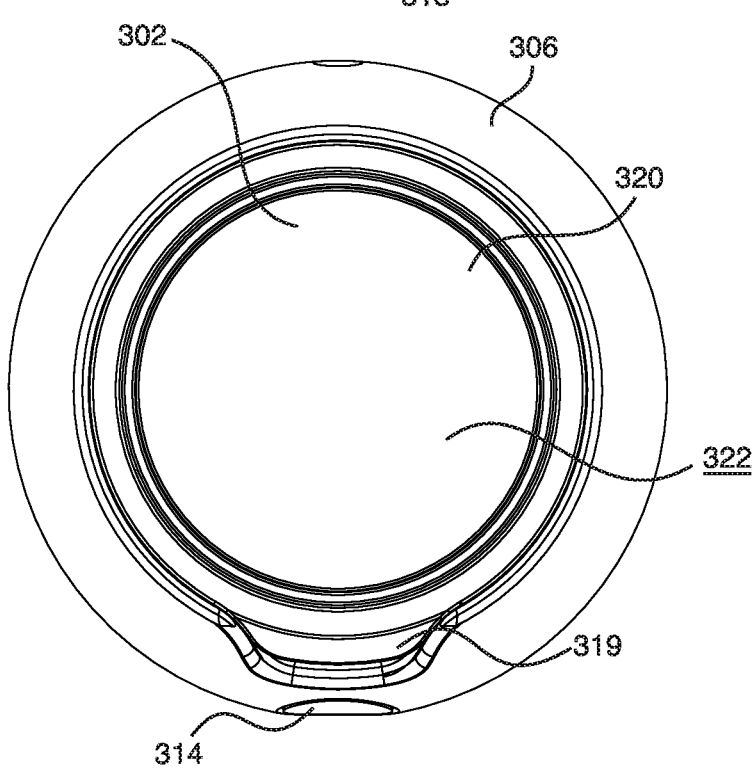
FIG. 20 is a top view of the skincare device illustrated in FIG. 13.
Figure 21:
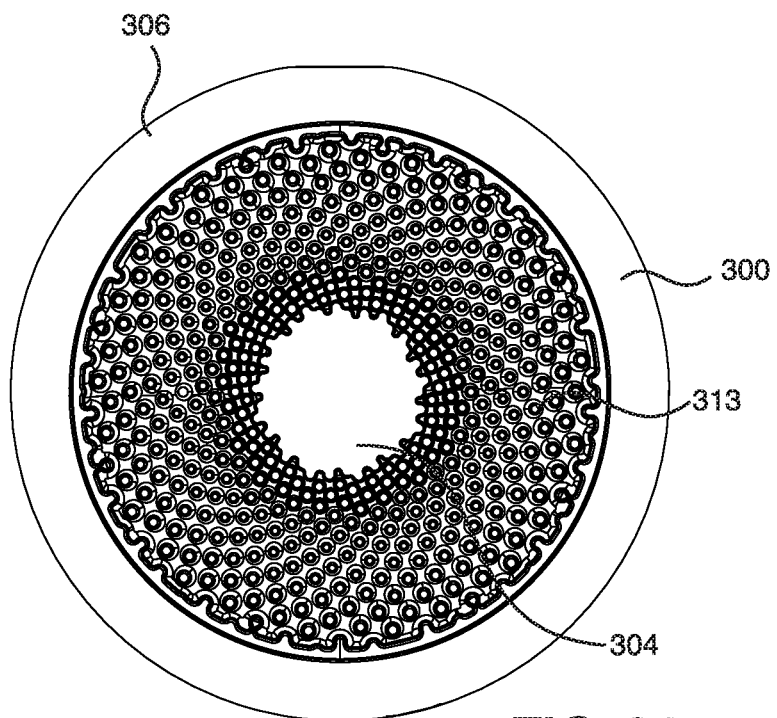
FIG. 21 is a bottom view of the skincare device illustrated in FIG. 13.
Figure 22:
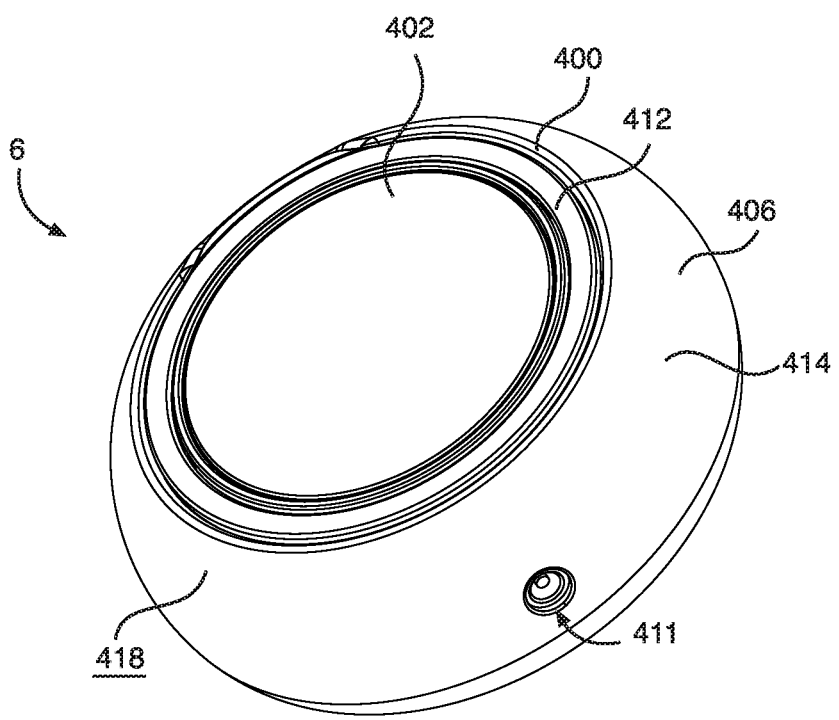
FIG. 22 is a perspective view of a third example skincare device.
Figure 23:
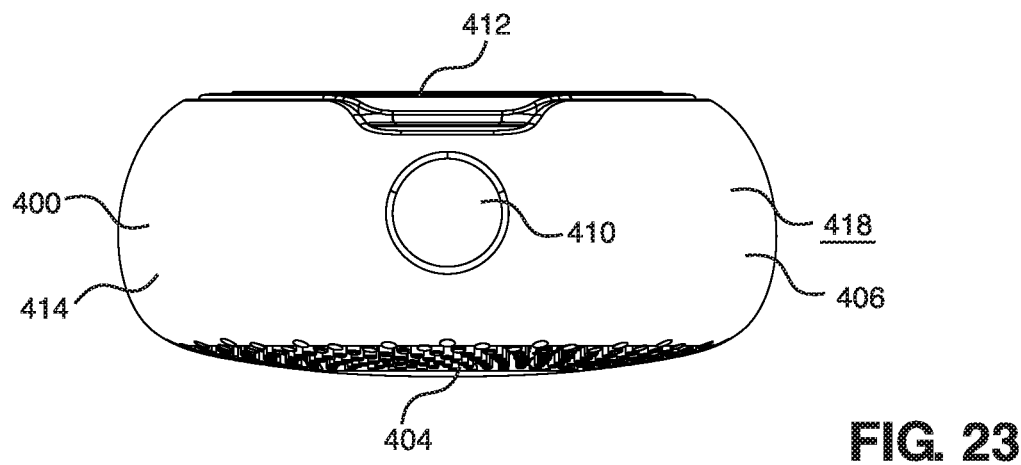
FIG. 23 is an end view of the skincare device illustrated in FIG. 22.
Figure 24:
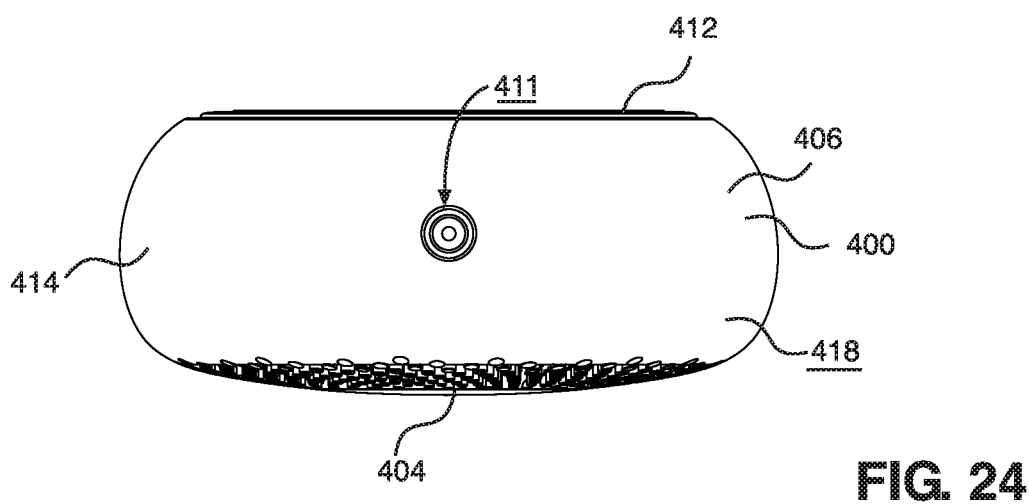
FIG. 24 is another end view of the skincare device illustrated in FIG. 22.
Figure 25:
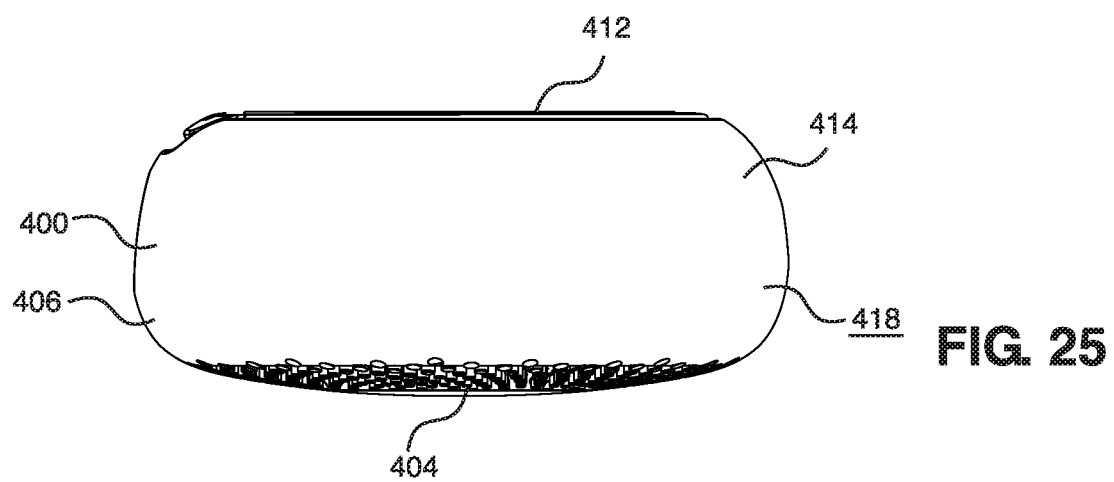
FIG. 25 is a side view of the skincare device illustrated in FIG. 22.
Figure 26:
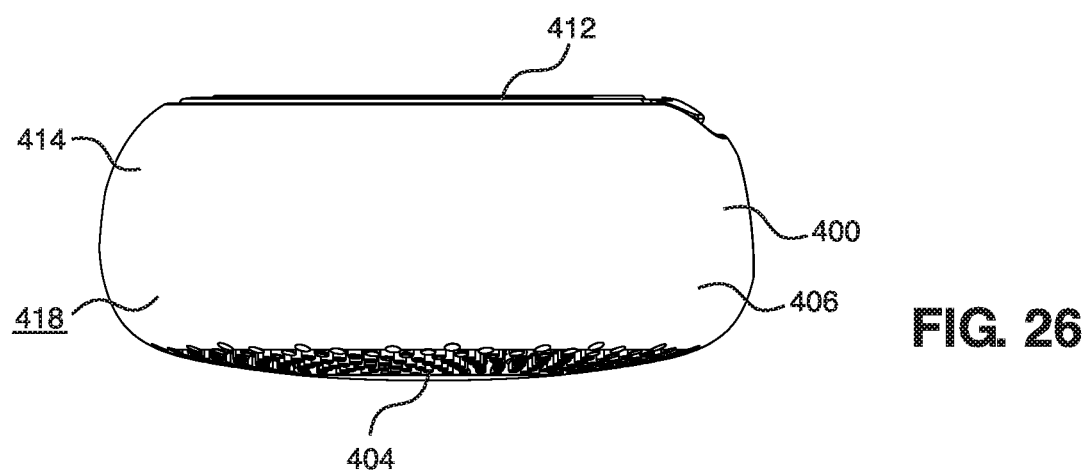
FIG. 26 is another side view of the skincare device illustrated in FIG. 22.
Figure 27:
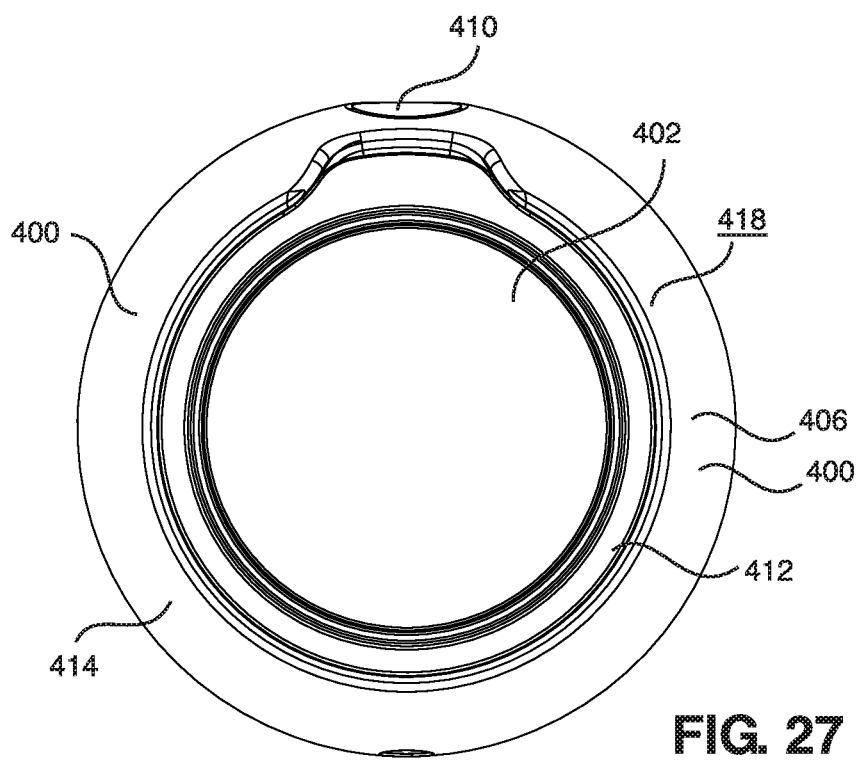
FIG. 27 is a top view of the skincare device illustrated in FIG. 22.
Figure 28:
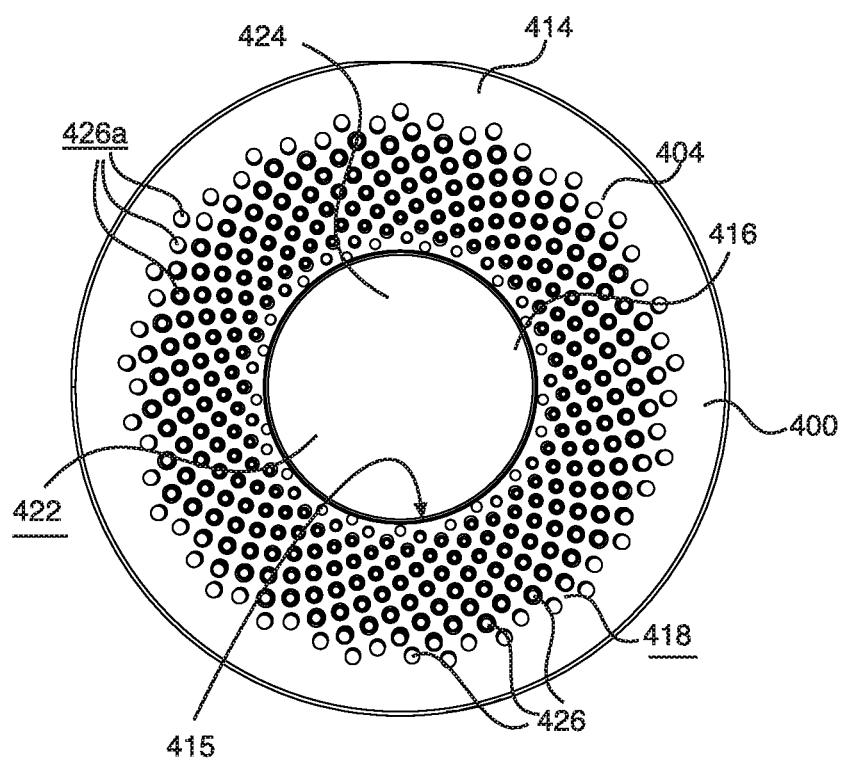
FIG. 28 is a bottom view of the skincare device illustrated in FIG. 22.

FIGS. 12A, 12B, 12C, 12D each illustrates a facial mask, such as facial mask 200, and the skincare device 2. FIG. 12A illustrates the skincare device 2 with the locking mechanism 50 removed from the groove 24 and the facial mask 200 disposed adjacent, but not in contact with the first side 20 of the skincare device 2. FIG. 12B illustrates the facial mask 200 in contact with the first side 20 and adjacent the groove 24 and the locking mechanism 50 disposed above, but not in contact with, the first side 20. FIGS. 12C and 12D each illustrates the facial mask 200 in contact with the first side 20, disposed partially within the groove 24, and being secured to the first side 20 by the locking mechanism 50, which itself is partially disposed within the groove 24.

In use, a user may place a mask, such as mask 200, in contact with the first side 20 and lock the mask into place via the locking mechanism 50, as is illustrated in FIGS. 12A, 12B, 12C, and 12D. The user then presses or holds the user control 72 of the skincare device 2 to activate the device. The skincare device 2 then signals to the user that the device is ready to be used. One such manner of signaling that the skincare device 2 is ready to be used is through the emission of light from the light source 100. The light source 100 can be configured such that it emits light for a certain pertain of time (one second, two seconds, three seconds etc.) to indicate that it is ready for use; it could also emit a certain color or sequence of colors to indicate that it is ready for use. In various other embodiments, the light source could emit light in a rotating fashion such that a certain light or lights follow a path to indicate that the device is ready for use. Optionally, once the device has been activated, a user may press and/or hold the user control 72 for a certain period of time to ensure that the skincare device 2 is able to communicate with a second device such as a mobile phone. An example of such a communication would be a series of flashing lights after a user presses and holds the user control for three seconds. Confirmation that the skincare device 2 is in communication with a second device could come in the form of another emission of light by the light source 100.

In one example, after activation of the device the user may select a certain mode, program, or treatment that the skincare device is configured to perform. The user may press the user control a number of times, which allows the skincare device to cycle through possible treatments which are communicated to the user via the light source. In an example embodiment, pressing the user control after activation could cycle result in the device emitting green, red, and/or blue light in some order. Other colors of light may also be emitted at this juncture. In such an embodiment, the user could press the user control again (or cease pressing the control) when the device emits a particular light which corresponds to the treatment the user prefers the device to perform (the user could find this information in a manual or through trial and error). The device would then perform the selected treatment pattern. In another embodiment, a particular treatment can be selected via additional buttons placed on the skincare device that allow the user to cycle through various treatments. In a different embodiment, a particular treatment method can be selected via the use of a second device that is configured to communicate with and transmit information to the skincare device, such as a mobile phone. In other embodiments, the speeds and/or rotational patterns of the light emitted by the light source could indicate various treatments to-be-selected by the user.

Once a particular treatment has been selected by a user, the skincare device 2 will do one or more of providing heat or cold therapy, emitting various types of light, and/or vibrating. The skincare device 2 may perform these treatments in any order, for any duration, and through contact with or placement near the skin via various portions of the device and as described above. Additionally, these treatments may be applied to the skin with or without the aid of a beauty accessory.

Various example treatment patterns are included, below. The following treatment patterns described are merely illustrative in nature and are not designed in any way to limit the contents of the disclosure. The following treatment patterns may include the use of a mask in conjunction with the device; accordingly, it is assumed that any mask used is secured on or partially within the skincare device in each treatment pattern prior to selection of a treatment pattern. Other examples exist in which masks are not used, however. Moreover, various skincare devices may perform a number of other treatment patterns that are not described below.

In each example treatment pattern, a user presses a user control of a skincare device, such as user control of skincare device. This activates the skincare device. Optionally, the user may then press and hold the user control for approximately three seconds; doing so will confirm that the skincare device is capable of communicating with a second device via approximately three seconds of flashing lights emitted by a light source, such as light source. The user then selects the first example treatment pattern, as described above, by pressing the user control at an appropriate time or in an appropriate manner. At this point, the user will place the skincare device adjacent or in contact with his or her skin, as the example treatment has been initiated. The various example treatment patterns, accordingly, will treat the skin of a user via the following patterns of heating, cooling, light emission, and/or vibration.

After selection of the first treatment pattern, the light source will first simultaneously emit red light and heat the first side of the skincare device. This will occur for approximately thirty seconds. Next, the skincare device will simultaneously heat the first side, emit red light, and vibrate for approximately sixty seconds. Thereafter, the skincare device will simultaneously vibrate and emit red light for approximately thirty seconds. This may be repeated for a number of cycles; in various treatment patterns, one, two, three, four, five, or more than five cycles may be used. The skincare device will then deactivate, as evidenced by three pulsations of the motor just prior to its deactivation. Deactivation of the skincare device may occur automatically at the end of a treatment pattern or via manipulation of the user control.

In various embodiments, the first example treatment pattern may comprise any number of actions which may be performed in any order. For example, the light source may emit any of green, blue, pink, or red light and may constantly emit said light; it may also emit light in any suitable interval, including intervals of one, two, three, five, ten, fifteen, twenty, thirty, sixty, or any other suitable number of seconds. Additionally, a first treatment may include a period in which the device does not emit light, heat, cool, or vibration. Various example first treatments may include any suitable number of cycles, as well. Moreover, in other example first treatments, the motor may produce vibrations and/or pulsations at any frequency and for any suitable length of time, including between about 5 and about 180 seconds, between about 30 and about 150 seconds, and between about 60 and about 120 seconds.

A second example treatment pattern also may be selected via the user control, as described above. After selection of the second treatment pattern, the skincare device will simultaneously emit red light and heat the first side of the skincare device. This will occur for approximately thirty seconds. Next, the skincare device will simultaneously heat the first side, emit red light, and vibrate or pulsate for approximately sixty seconds. Thereafter, the device shall emit green light and vibrate simultaneously for approximately thirty seconds. The skincare device will then deactivate, as evidenced by three pulsations of the motor just prior to cessation of function. Deactivation of the skincare device may occur automatically at the end of a treatment pattern or via manipulation of the user control. Optionally, the motor may then be reactivated and produce vibrations and/or pulsations of the skincare device for an additional thirty seconds; the strength of the vibrations and/or pulsations may decrease as this time passes.

In various embodiments, the second example treatment pattern may comprise any number of actions which may be performed in any order. For example, the light source may emit any of green, blue, pink, or red light and may constantly emit said light; it may also emit light in any suitable interval, including intervals of one, two, three, five, ten, fifteen, twenty, thirty, sixty, or any other suitable number of seconds. Additionally, a second treatment may include a period in which the device does not emit light, heat, cool, or vibrate. Various example second treatments may include any suitable number of cycles, as well. Moreover, in other example second treatments, the motor may produce vibrations and/or pulsations at any frequency and for any suitable length of time, including between about 5 and about 180 seconds, between about 30 and about 150 seconds, and between about 60 and about 120 seconds.

A third example treatment pattern also may be selected via the user control, as described above. After selection of the third treatment pattern, the skincare device will simultaneously emit blue light and heat the first side of the skincare device. This will occur for approximately sixty seconds. Next, the skincare device will simultaneously cool the first side, emit blue light, and emit vibrations for approximately thirty seconds. Finally, the skincare device will simultaneously cool the first side, emit red and blue light, and vibrate for approximately thirty seconds. Deactivation of the skincare device may occur automatically at the end of a treatment pattern or via manipulation of the user control. Optionally, the motor may then be reactivated and produce vibrations and/or pulsations of the skincare device for an additional thirty seconds.

In various embodiments, the third example treatment pattern may comprise any number of actions which may be performed in any order. For example, the light source may emit any of green, blue, pink, or red light and may constantly emit said light; it may also emit light in any suitable interval, including intervals of one, two, three, five, ten, fifteen, twenty, thirty, sixty, or any other suitable number of seconds. Additionally, a third treatment may include a period in which the device does not emit light, heat, cool, or vibrate. Various example third treatments may include any suitable number of cycles, as well. Moreover, in other example third treatments, the motor may produce vibrations and/or pulsations at any frequency and for any suitable length of time, including between about 5 and about 180 seconds, between about 30 and about 150 seconds, and between about 60 and about 120 seconds.

A fourth example treatment pattern also may be selected via the user control, as described above. After selection of the fourth treatment pattern, the light source will first simultaneously emit red light, cool, and emit vibrations to the first side of the skincare device. This will occur for approximately thirty seconds. Next, the skincare device will simultaneously emit red light, cool, and emit vibrations to the first side for approximately thirty seconds. The motor will vibrate at a low frequency at this time. After this, the skincare device will simultaneously emit blue light, cool, and emit vibrations to the first side for approximately thirty seconds. The skincare device will then deactivate, as evidenced by three pulsations of the motor just prior to cessation of function. Deactivation of the skincare device may occur automatically at the end of a treatment pattern or via manipulation of the user control. Optionally, the motor may then be reactivated and produce vibrations and/or pulsations of the skincare device for an additional thirty seconds.

In various embodiments, the fourth example treatment pattern may comprise any number of actions which may be performed in any order. For example, the light source may emit any of green, blue, pink, or red light and may constantly emit said light; it may also emit light in any suitable interval, including intervals of one, two, three, five, ten, fifteen, twenty, thirty, sixty, or any other suitable number of seconds. Additionally, a fourth treatment may include a period in which the device does not emit light, heat, cool, or vibrate. Various example fourth treatments may include any suitable number of cycles, as well. Moreover, in other example fourth treatments, the motor may produce vibrations and/or pulsations at any frequency and for any suitable length of time, including between about 5 and about 180 seconds, between about 30 and about 150 seconds, and between about 60 and about 120 seconds.

A fifth example treatment pattern also may be selected via the user control, as described above. After selection of the fifth treatment pattern, the skincare device will simultaneously emit red light, heat the first side of the skincare device, and pulsate at a high frequency. This will occur for approximately thirty seconds. The skincare device will then simultaneously heat the first side, emit red light, and vibrate or pulsate for approximately sixty seconds. The motor shall vibrate at a low frequency for this time period. Next, the skincare device will then produce vibrations for thirty seconds that gradually decrease in strength during said time period. The skincare device will then deactivate, as evidenced by three pulsations of the motor just prior to cessation of function. Deactivation of the skincare device may occur automatically at the end of a treatment pattern or via manipulation of the user control.

In various embodiments, the fifth example treatment pattern may comprise any number of actions which may be performed in any order. For example, the light source may emit any of green, blue, pink, or red light and may constantly emit said light; it may also emit light in any suitable interval, including intervals of one, two, three, five, ten, fifteen, twenty, thirty, sixty, or any other suitable number of seconds. Additionally, a fifth treatment may include a period in which the device does not emit light, heat, cool, or vibrate. Various example second treatments may include any suitable number of cycles, as well. Moreover, in other example fifth treatments, the motor may produce vibrations and/or pulsations at any frequency and for any suitable length of time, including between about 5 and about 180 seconds, between about 30 and about 150 seconds, and between about 60 and about 120 seconds.

A sixth example treatment pattern also may be selected via the user control, as described above. After selection of the sixth treatment pattern, the skincare device will simultaneously emit red light and heat the first side of the skincare device. This will occur for approximately thirty seconds. Next, the skincare device will simultaneously heat the first side, vibrate and emit red light for approximately thirty seconds. After this, the skincare device will simultaneously emit green light and vibrate for approximately thirty seconds. Next, the skincare device will then produce vibrations for thirty seconds that gradually decrease in strength across said time period. The skincare device will then deactivate, as evidenced by three pulsations of the motor just prior to cessation of function. Deactivation of the skincare device may occur automatically at the end of a treatment pattern or via manipulation of the user control.

In various embodiments, the sixth example treatment pattern may comprise any number of actions which may be performed in any order. For example, the light source may emit any of green, blue, pink, or red light and may constantly emit said light; it may also emit light in any suitable interval, including intervals of one, two, three, five, ten, fifteen, twenty, thirty, sixty, or any other suitable number of seconds. Additionally, a sixth treatment may include a period in which the device does not emit light, heat, cool, or vibrate. Various example second treatments may include any suitable number of cycles, as well. Moreover, in other example sixth treatments, the motor may produce vibrations and/or pulsations at any frequency and for any suitable length of time, including between about 5 and about 180 seconds, between about 30 and about 150 seconds, and between about 60 and about 120 seconds.

Various other example treatment patterns exist. In such patterns, various skincare devices may emit light, heat and/or cool, and vibration/pulsate for any duration, in any order, and at any strength.

FIGS. 13, 14, 15, 15A, 16, 17, 18, 19, 20, and 21 illustrate another example skincare device 4. This skincare device is similar to the skincare device 2 shown in FIGS. 1 through 9, except as described below. Thus, the skincare device 4 comprises at least a main body 300, a first side 302, a second side 304, an intermediate portion 306, a controller 307, a light source 308, a power source 309, a motor 310, a temperature control unit 312, a temperature exchange component 313, a user control 314, a frame 315, a charging port 316, first and second temperature sensors 317, 318, and a locking mechanism 319.

In the illustrated embodiment, the first side 302 includes contact piece 320 having a surface 322 that a user will contact when the skincare device 4 is in use. The contact piece 320 is comprised of metal in the illustrated embodiment and is configured to transmit heat therapy and/or cool therapy to a user. The portion of the skincare device 4 that a user contacts to receive such therapies is not a portion of the panel 324 that houses a power source 326; this differs from the skincare device 2 described above, in which the upper portion 66 of the panel 62 defines a surface 22 of the first side 20 that a user contacts to receive heat and/or cool therapy. To be clear, though the contact piece 320 may be disposed substantially adjacent the panel 324 in the illustrated embodiment, these components are not integrally formed. A skilled artisan will be able to select a suitable contact piece according to a particular example based on various configurations, including the sizes and shapes of the components housed within the skincare device. In various embodiments, the contact piece may comprise any suitable material(s), including one or more of aluminum, an aluminum alloy, a zinc alloy, copper, stainless steel, gold, silver, ceramic, and other suitable materials. In other embodiments, a portion of the contact piece may be coated with a thermal film or paste. In different embodiments, the surface of the contact piece may have a diameter between about 1 cm and about 15 cm, between about 2 cm and about 10 cm, and between about 3 and about 6 cm.

The contact piece 320 also includes first and second legs 328, 330 at a distal end 332 of the contact piece 320 opposite its surface 322 that is contacted by a user. The first and second legs 328, 330 form a cavity 334 into which the temperature control unit 312 may be placed. Placing the temperature control unit 312 within the cavity 334 allows for the temperature control unit 312 to be disposed directly adjacent the surface 322 a user contacts to receive heat therapy and/or cool therapy. Such placement allows for the efficient and effective transmission of heat therapy and/or cool therapy to the user via the surface 322 because the contact piece 320 is so near the surface 322. A skilled artisan will be able to select a suitable contact piece based on various considerations, including the shape and size of the temperature control unit. In other embodiments, an intermediary may be placed between the contact piece and the temperature control unit. In different embodiments, the contact piece may include zero, one, three, or more than three legs. In alternative embodiments, the contact piece may not define a cavity and the temperature control unit may be secured to the contact piece via an adhesive, a mechanical attachment, or some other mechanism.

Finally, the temperature exchange component 313 directly attaches to or connects with the frame 315 in the illustrated embodiment. This embodiment does not include a support member, as was included in skincare device 2.

FIGS. 22, 23, 24, 25, 26, 27, and 28 illustrate another example skincare device 6. This skincare device 6 is similar to the skincare device 4 shown in FIGS. 13 through 21, except as described below. Thus, the skincare device 6 comprises at least a main body 400 having a first side 402, a second side 404, an intermediate portion 406, a light source (not illustrated in the Figures), a motor (not illustrated in the Figures), temperature control unit (not illustrated in the Figures), a user control 410, a charging port 411, and a locking mechanism 412.

In this embodiment, the skincare device 6 is partially covered by a silicone cover 414. More specifically, the silicone cover 414 extends such that it that forms a portion of the second side 404 and the intermediate portion 406. The exterior surface 418 of the silicone cover 414 comprises a least a portion of the surfaces of the second side 404 and intermediate portion 406. The silicone cover 414 is a unitary piece in the illustrated embodiment.

The silicone cover 414 also defines a cutout 415 about the center portion 424 of the second side 404. The cutout 415 is substantially circular in shape. The center portion 424 is substantially circular in shape and allows for the temperature exchange component 416 to be touched by a user; in particular, a second exterior surface 422 of the second side 404 comprises a portion of the temperature exchange component 416 that may be contacted by a user. The temperature exchange component 416 may be comprised of any material that may comprise the temperature exchange component 112 described above. The temperature exchange 416 component may also display a logo or symbol.

The exterior surface 418 of the silicone cover 414 that comprises a portion of the second side 404 defines a set of protrusions 426 which extend away from the first side 402. Each protrusion of the set of protrusions 426 is integrally formed with the second side 404 (and, thus, the silicone cover 414) in the illustrated embodiment. Each protrusion of the set of protrusions 426 is comprised of the same material as the exterior surface 418 in the illustrated embodiment, as well. However, in other embodiments, the set of protrusions may be attached to the second side and/or silicone covering via any mechanical attachment and/or via the use of an adhesive. Alternatively, some protrusions of the set of protrusions may be integrally formed with the second side and/or silicone covering and others may be attached to the second side and/or silicone covering in other embodiments.

Each protrusion of the set of protrusions 426 includes an upper surface 426a, which defines a diameter. In the illustrated embodiment, the diameters of the various upper surfaces 426a are not uniform. Generally, upper surfaces 426a of the protrusions of the set of protrusions 426 nearer the center portion 424 have smaller diameters than do the upper surfaces 426a of the protrusions of the set of protrusions 426 further from the center portion 424. In various embodiments, however, the set of protrusions may be comprised of any material and may have any alignment. A skilled artisan will be able to select suitable protrusion material(s) and alignment according to a particular example based on various considerations, including the size and shape of the second side and the functionality of the device. In various embodiments, the protrusions may be comprised of any suitable material. In other embodiments, the protrusions may be coated with gold, nickel, platinum, and/or another similar material. In different embodiments, some protrusions may be comprised of a first material, while other protrusions are comprised of a second material. In various other embodiments, any portion of the second side may include protrusions, including between about 5% and about 90% of the surface of the second side, between about 25% and about 70% of the surface of the second side, and between about 40% and about 55% of the surface of the second side. In various embodiments, one or more protrusion of the set of protrusions may have a height between about 0.1 mm and about 6 cm, a height between about 2 mm and about 3 cm, and a height between about 5 mm and about 1 cm. In various embodiments, one or more protrusion of the set of protrusions may have a diameter between about 0.01 mm and about 5 cm, a diameter between about 0.1 mm and about 2.5 cm, and a diameter between about 0.5 mm and about 1 cm.

In addition, the skincare device 6 illustrated in FIGS. 22 through 28 includes a temperature control unit that is not capable of providing cool therapy. Indeed, in the illustrated embodiment, the temperature control unit is merely capable of heating the first side 402 of the device via releasing heat towards the same and cannot reduce its temperature. The skincare device 6, however, is still capable of emitting vibrations via the motor and a number of different colors of light (including red, green, and blue) from the light source 408. In a different embodiment, however, the temperature control unit may be capable of reducing the temperature of the first side 402 and providing cooling therapy via the same.

Figure 29:
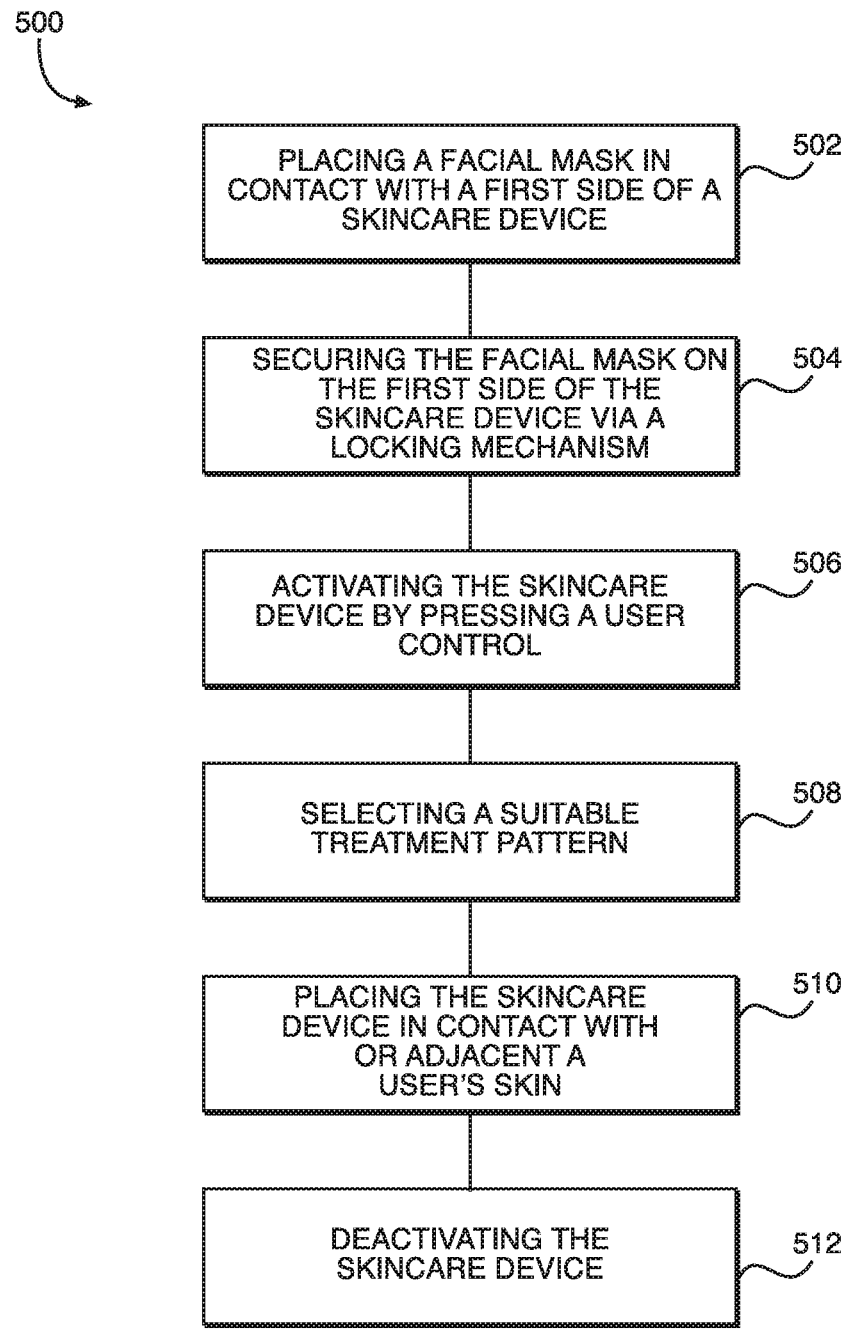
FIG. 29 is a flowchart representation of an example method of using a skincare device and a beauty accessory.

FIG. 29 is a flowchart representation of an example method 500 of using a skincare device and a mask. Performance of this method results in the treatment of the user's body, such as the face and/or neck, by a skincare device and a beauty accessory. This method can be used for treating any portion of a human body.

An initial step 502 comprises placing a beauty accessory, such as facial mask 200, in contact with the first side of a skincare device, such as the first side 20 of skincare device 2. In various other methods, any suitable beauty accessory and/or skincare device may be selected, including skincare device 4 and/or skincare device 6. In different methods, one or more beauty accessories may be placed in contact with the first side simultaneously.

Another step 504 comprises securing the facial mask 200 on the first side 20 of the skincare device 2 via a locking mechanism, such as locking mechanism 50. The locking mechanism 50 is placed over the facial mask 200 and is inserted, along with a portion of the mask 200, within a groove, such as groove 24. In various other embodiments, the facial mask may be secured to the skincare device 2 via any physical mechanism or via an adhesive.

Another step 506 comprises activating the skincare device 2 by pressing a user control, such as user control 72, in order to ready the skincare device 2 for use.

Another step 508 comprises selecting a suitable treatment pattern, such as any of treatment patterns one, two, three, four, five, or six described above, or any other suitable treatment pattern. A treatment pattern may be selected via the user control 72. Selection of a particular treatment pattern may be communicated to a user via a light source, such as light source 100, which may emit different patterns, colors, or flashes of light to indicate the various treatment patterns.

Another step 510 comprises placing the skincare device 2 in contact with or adjacent the user's skin. Doing so allows the skincare device 2 to treat the skin via the light emitted by the light source 100, vibrations and/or pulsations emitted by a motor, such as motor 80, and/or heating and/or cooling generated by a temperature control unit, such as temperature control unit 110.

Another step 512 comprises deactivating the skincare device 2. The skincare device 2 will indicate that deactivation has been initiated by pulsating a number of times, for a certain duration, or in particular pattern or by emitting light a certain number of times, for a certain duration, in a particular pattern, or by the emission of light of one or more particular colors. Deactivation of the skincare device 2 may occur automatically at the end of a treatment pattern or via manipulation of the user control 72.

It is noted that it is advantageous to complete this method 500 in the order illustrated and described. However, any order is considered suitable.

Figure 30:
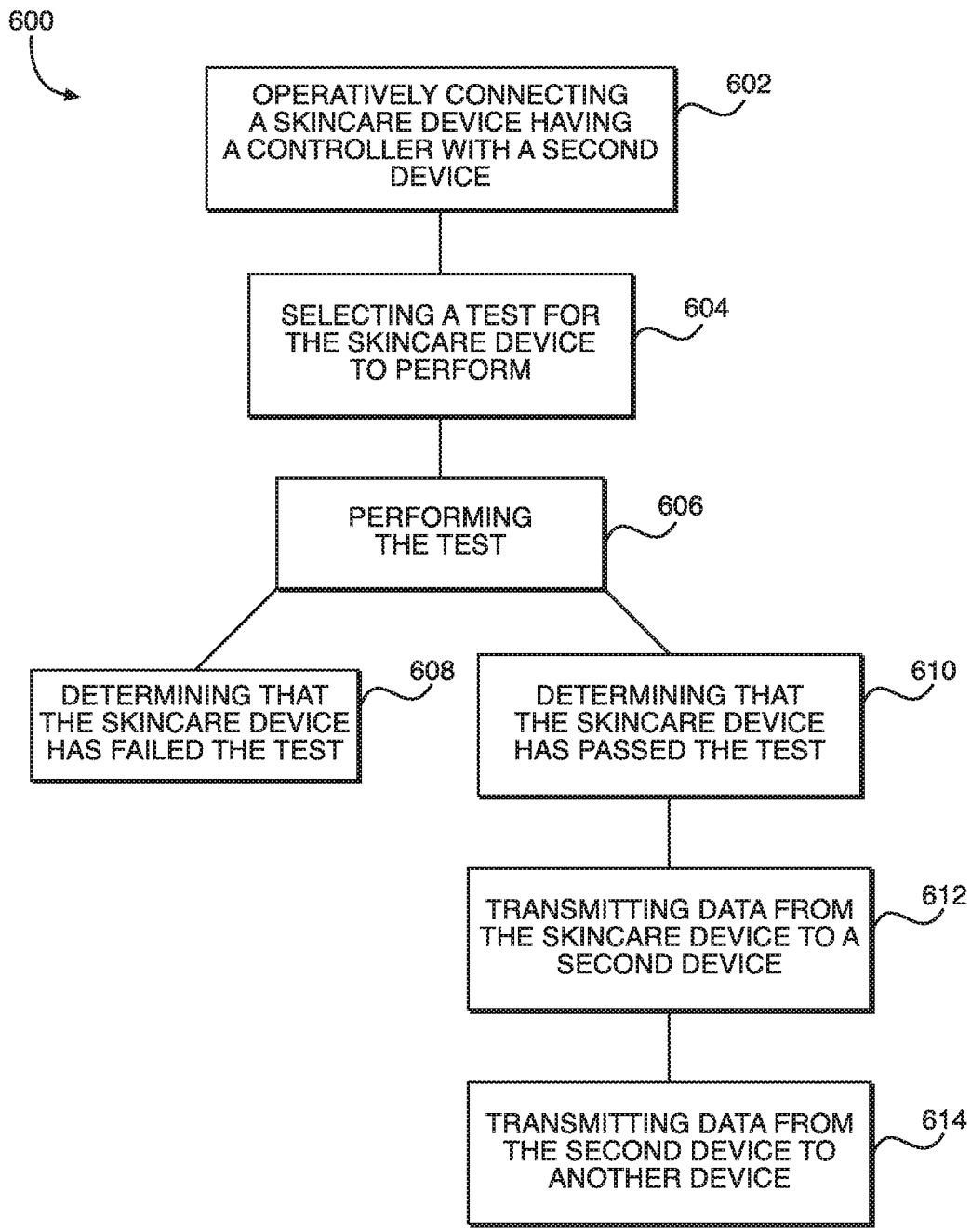
FIG. 30 is a flowchart representation of an example method of verifying authenticity of a skincare device.

FIG. 30 is a flowchart representation of an example method 600 of verifying authenticity of a skincare device. Performance of the method results in the confirmation or denial of a particular skincare device's authenticity.

An initial step 602 comprises operatively connecting a skincare device having a controller, such as skincare device 2 having controller 70, with a second device such as a personal computer, tablet, server, and/or mobile phone, for example. Any suitable skincare device and/or controller may be used, however, in other embodiments, including skincare device 4 and/or skincare device 6. The connection may be made wirelessly or via a wired connection.

Another step 604 comprises the second device selecting a particular test for the skincare device to perform. Such tests may include one or more of: a motor test, a battery test, a temperature control unit test, and/or a light source test in various embodiments. Any suitable test may be performed, though, in other embodiments.

Another step 606 comprises performing the test and/or test(s) selected in step 604.

Another step 608 comprises determining that the skincare device and/or its controller has failed the test(s) performed in step 606. In such an instance, the skincare device will be prevented from sending information pertaining to the skincare device to the second device. In other embodiments, the skincare device may be temporarily or permanently disabled after failure to perform the test(s).

Another step 610 comprises determining that the skincare device and/or its controller has passed the test(s) performed in step 606.

Another step 612 comprises transmitting data from the skincare device to the second device. The data transmitted generally contains information pertaining to the skincare device and may include one or more of the following: the skincare device's Chip ID, Information pertaining to the battery of the skincare device, the Media Access Control ("MAC") Address of the skincare device, and/or the serial number of the skincare device. Any pertinent information may be passed to the second device, however, in various embodiments.

Optionally, another step 614 comprises transmitting data from the second device to an additional device. The additional device may include one or more of: a personal computer, tablet, mobile phone, database, server, and/or other suitable devices.

It is noted that it is advantageous to complete this method 600 in the order illustrated and described. However, any order is considered suitable.

In all examples, a skincare device and its various components may be formed of any suitable material, including presently known and later-developed materials. A skilled artisan will be able to select appropriate materials for an example skincare device based on various considerations, including the size and shape of the skincare device, the motor housed within the skincare device, the light source housed within the skincare device, and the particular temperature control unit used.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A skincare device configured to treat the skin of a user, comprising:
   a main body having a first side having a first surface, a second side substantially opposite the first side having a second surface, and an intermediate portion extending from the first side to the second side having a third surface, the main body being substantially disc-shaped;
   a light source disposed within the main body and configured to emit light to treat said skin, the light source configured to emit the light adjacent the first side;
   a motor disposed within the main body and configured to produce pulsations of said skincare device;
   a temperature control unit disposed within the main body, the temperature control unit configured to generate heat to treat said skin and transfer the heat to the first side;
   a user control disposed on the intermediate portion, the user control configured to operate the light source, the motor, and the temperature control unit; and
   a power source disposed within the main body, said power source comprising a lithium-ion battery;
   wherein the first side and the intermediate portion cooperatively define a groove into which the light source emits the light.

2. The skincare device of claim 1, wherein the light source comprises light-emitting diode ("LED") lights.

3. The skincare device of claim 2, wherein the light source is configured to emit red light.

4. The skincare device of claim 3, wherein the light source is configured to emit green light.

5. The skincare device of claim 4, wherein the light source is configured to emit blue light.

6. The skincare device of claim 1, wherein the second surface defines a set of protrusions.

7. The skincare device of claim 1, further comprising a sensor disposed within the main body configured to detect the temperature of the skincare device and shut down the skincare device in the event that it exceeds a certain temperature.

8. The skincare device of claim 1, further comprising a controller disposed within the main body and an interface operatively connected to the controller, the interface being configured to transmit information to a mobile phone.

9. The skincare device of claim 1, wherein the third surface is comprised of silicone.

10. The skincare device of claim 9, wherein a portion of the second surface is comprised of silicone and is integrally formed with the third surface.

11. A skincare device configured to treat the skin of a user, comprising:
    a main body having a first side having a first surface, a second side substantially opposite the first side having a second surface, and an intermediate portion extending from the first side to the second side having a third surface, the first side and the intermediate portion defining an annular groove extending toward the second side, the second surface defining a set of protrusions comprised of metal, the third surface comprising silicone, the main body being substantially disc-shaped;
    a light source disposed within the main body and configured to emit light to treat said skin, the light source configured to emit the light adjacent the first side, the light source comprising an LED light;
    a motor disposed within the main body configured to produce pulsations of said skincare device;
    a temperature control unit disposed within the main body, the temperature control unit configured to generate heat to treat said skin and to transfer the heat to the first side, the temperature control unit configured to cool the first side of the main body in order to treat said skin;
    a controller disposed within the main body and an interface operatively connected to the controller, the interface being configured to transmit information; and
    a user control disposed on the intermediate portion, the user control configured to operate the light source, the motor, and the temperature control unit;
    wherein the first side and the intermediate portion cooperatively define a groove into which the light source emits the light.

12. The skincare device of claim 11, wherein light source is configured to emit red, green, and blue light.

* * * * *